US008765138B2

(12) United States Patent
Stamets

(10) Patent No.: US 8,765,138 B2
(45) Date of Patent: Jul. 1, 2014

(54) ANTIVIRAL AND ANTIBACTERIAL ACTIVITY FROM MEDICINAL MUSHROOMS

(76) Inventor: Paul Edward Stamets, Shelton, WA (US)

(*) Notice: Subject to any disclaimer, the term of this patent is extended or adjusted under 35 U.S.C. 154(b) by 1183 days.

(21) Appl. No.: 12/284,646

(22) Filed: Sep. 24, 2008

(65) Prior Publication Data

US 2009/0130138 A1 May 21, 2009

Related U.S. Application Data

(63) Continuation-in-part of application No. 11/728,613, filed on Mar. 27, 2007, which is a continuation-in-part of application No. 11/386,402, filed on Mar. 22, 2006, now abandoned, which is a continuation-in-part of application No. 11/145,679, filed on Jun. 6, 2005, now abandoned, which is a continuation-in-part of application No. 11/029,861, filed on Jan. 4, 2005, now abandoned.

(60) Provisional application No. 60/994,972, filed on Sep. 24, 2007, provisional application No. 60/534,776, filed on Jan. 6, 2004.

(51) Int. Cl.
*A61K 36/06* (2006.01)
*A61K 36/09* (2006.01)

(52) U.S. Cl.
USPC .................................................... 424/195.15

(58) Field of Classification Search
None
See application file for complete search history.

(56) References Cited

PUBLICATIONS

Pegler, D.N. "Useful Fungi of the World: Agaricum—the 'universal remedy' of ancient Rome". Mycologist, vol. 14, Part 4 (Nov. 2000) pp. 146-147.*

Moore et al. "Fungal Products as Food" pp. 1-17. Reprint of Moore, D. & Chiu, S. W. Fungal products as food. Chapter 10 in Bio-Exploitation of Fkilamentous Fungi (ed S.B. Pointing & K. D. Hyde), pp. 223-251. Fungal Diversity Press: Hong Kong.*

"Tinctura Cinchonae Compsita" from King's American Dispensatory, 1898. Retrieved from: Henriette's Herbal Homepage on May 2, 2012. Retrieved from: <URL: http://www.henriettesherbal.com/eclectic/kings/cinchona_tinc1.html>.*

Schar, D. Plant botanic. Retrieved from the Internet on: May 2, 2012. Retrieved from: <URL: http://www.planetbotanic.ca/maitake_journal_materia.htm>.*

"Alcohol.-Alcohol, U.S.P". From: A Handbook of Useful Drugs, by State Medical Examining and Licensing Boards, Press of the American Medical Association: 1913.Retrieved from the Internet on: May 2, 2012. Retrieved from the Internet: <URL: http://chestofbooks.com/health/materia-medica-drugs/American-Medical-Association/A-Handbook-of-Useful-Drugs>.*

Hobbs, C. Medicinal Mushrooms (Herbs and Health Series). Feb. 1, 2002. Retrieved from the Internet on: May 2, 2012. Retrieved from: <URL: http://www.naturalpedia.com/Tuberculosis-11.html>.*

Stamets, P. "Novel Antimicrobials from Mushrooms". HerbalGram. 2002;54:28-33.*

Moore et al. "Fungal Products as Food" pp. 1-17. Reprint of Moore, D. & Chiu, S. W. Fungal products as food. Chapter 10 in Bio-Exploitation of Fkilamentous Fungi (ed S.B. Pointing & K. D. Hyde), (2001), pp. 223-251. Fungal Diversity Press: Hong Kong.*

* cited by examiner

*Primary Examiner* — Amy L Clark
(74) *Attorney, Agent, or Firm* — William R. Hyde

(57) ABSTRACT

Compounds having unique antiviral and antibacterial properties are prepared from medicinal mushroom mycelium, extracts and derivatives. The compositions are derived from *Fomitopsis, Piptoporus, Ganoderma, Inonotus, Trametes, Pleurotus*, and blends of medicinal mushroom species and are useful in preventing and treating viruses including Poxyiridae and Orthopox viruses, flu viruses including bird flu (H5N1), SARS and Hepatitis C (HCV), as well as infections from *Mycobacterium tuberculosis, Staphylococcus aureus* and *Escherichia coli.*

17 Claims, 6 Drawing Sheets

ANTIVIRAL AND ANTIBACTERIAL ACTIVITY FROM MEDICINAL MUSHROOMS

BACKGROUND OF THE INVENTION

1. Field of the Invention

The present invention relates to methods and products useful in restricting the growth, spread and survivability of viruses and bacteria in animals, especially humans. More particularly, the invention relates to methods and medicinal mushroom mycelium products for treating Herpes, Orthopox, influenza, SARS, Hepatitis, Tuberculosis, *Escherichia coli* and *Staphylococcus aureus* and other viruses and bacteria.

2. Description of the Related Art

Despite advances in modern medicine, microbes and viruses continue to kill millions of people, stimulating the search for new antimicrobial and antiviral agents, some of which have proven to be of significant commercial value. A major difficulty in the discovery of antimicrobial and antiviral agents is their inherent toxicity to the affected host organism. For instance, a novel agent or treatment that kills the virus but also harms the human host is neither medically practicable nor commercially attractive. Hence, many new antiviral drugs have never made it past preliminary screening studies as they have failed to prove non-toxicity and are unsafe to consume.

That medicinal mushrooms have been ingested for hundreds, and in some cases, thousands of years, is strong support for their non-toxicity, making them appealing candidates in the search for new antimicrobial and antiviral agents. The cell surface of mycelium secretes antibiotics in a kind of "sweat" which are known in the field as exudates or secondary metabolites. These antibiotics and enzymes target distinct sets of microbes. Useful antibiotics isolated from mushrooms include calvacin from the Giant Puffball (*Calvatia gigantea*), armilliaric acid from Honey Mushrooms (*Armillaria mellea*), campestrin from *Agaricus campestris* (The Meadow Mushroom), coprinol from Inky Caps (*Coprinus* species) corolin from Turkey Tail Mushrooms (*Trametes versicolor=Coriolus versicolor*), cortinellin from Shiitake (*Lentinula edodes*), ganomycin from Reishi (*Ganoderma lucidum*) and sparassol from Cauliflower mushrooms (*Sparassis crispa*).

Suzuki et al. (1990) characterized an antiviral water-soluble lignin in an extract of the mycelium of Shiitake mushrooms (*Lentinula edodes*) isolated from cultures grown on rice bran and sugar cane bagasse which limited HIV replication in vitro and stimulated the proliferation of bone-marrow cells. Clinical trials with lentinan in the treatment of HIV patients showed inhibitory activity. (Gordon et al., 1998). However, Abrams (2002) found no significant advantage in using lentinan in treating AIDS patients. Another mushroom recognized for its antiviral activity is *Fomes fomentarius*, a hoof-shaped wood conk growing trees, which inhibited the tobacco mosaic virus (Aoki et al., 1993). Collins & Ng (1997) identified a polysaccharopeptide inhibiting HIV type 1 infection from Turkey Tail (*Trametes versicolor*) mushrooms while Sarkar et al. (1993) identified an antiviral substance resident in an extract of Shiitake (*Lentinula edodes*) mushrooms. More recently, derivatives of the Gypsy mushroom, *Rozites caperata*, were found by Piraino & Brandt (1999) to have significant inhibition against the replication and spread of *varicella zoster* (the 'shingles' and 'chickenpox' virus), influenza A, and the respiratory syncytial virus (RSV) but not against HIV and other viruses. Eo et al. (1999) found antiviral activity from the methanol-soluble fractions of Reishi mushrooms (*Ganoderma lucidum*), selectively inhibiting Herpes simplex and the vesicular stomatitus virus (VSV). Wang & Ng (2000) isolated a novel ubiquitin-like glycoprotein from Oyster mushrooms (*Pleurotus ostreatus*) that demonstrated inhibitory activity toward the HIV-1 reverse transcriptase. Arabinoxylane inhibits HIV indirectly through the enhancement of NK cells that target the virus. Arabinoxylanes are created from mushroom mycelia's enzymatic conversion of rice bran (Ghoneum, M., 1998). Research by Dr. Byong Kak Kim showed that extracts of Reishi (*Ganodenna lucidum*) prevented the death of lymphocytes infected with HIV and inhibited the replication of the virus within the mother and daughter cells (Kim et al., 1994). In response to hot water extracts of Reishi mushrooms, preserved in ethanol, versus saline controls, NK cell activity was significantly augmented when cancer cells were co-cultured with human spleen cells. (Ohmoto, 2002). A mycelial combination of 7 species grown on rice achieved a similar result, greater than any one species at the same dosage. As the water extract of the fruitbodies is high in beta glucans while the mycelium-on-rice is low in beta glucans, but is high in arabinoxylanes, two causal agents are identified as NK effectors. Both the extract and the heat treated, freeze dried, powdered mycelium from 7 species share common activity levels of enhancing NK activity by 300+%. These compounds may be synergistic. This same combination of 7 species fermented on rice had a strong effect against HIV, inhibiting replication by 99% while the water extract of Reishi fruitbodies was 70%, respectively. These results underscore that water extractions of fruitbodies and oral administration of myceliated rice positively influence the immune system, activating different subsets of immunological receptor sites. Maitake (*Grifola frondosa*) is currently the subject of research in the treatment of HIV. Mizuno et al. (1996) noted that crude fractions from Chaga (*Inonotus obliquus*) showed antiviral activity against HIV.

*Fomitopsis officinalis* (Villars) Bondarzew & Singer (=*Agaricum officinalis, Fomes officinalis, Fomes laricis* and *Laricifomes officinalis*) has the common names Agarikon, Quinine Conk, Larch Bracket Mushroom, Brown Trunk Rot, Eburiko, Adagan ('ghost bread') and Tak'a di ('tree biscuit'). Once widespread throughout the temperate regions of the world, this perennial wood conk saprophytizes larch, Douglas fir and hemlock, preferring mature woodlands. Now nearly extinct in Europe and Asia, this mushroom is a resident of the Old Growth forests of Northern California, Oregon, Washington and British Columbia. Known constituents include beta glucans, triterpenoids and agaricin. Forms used include mushroom fruitbodies and mycelium. *F. officinalis* has traditionally been used for centuries for the treatment of "coughing illnesses." Mizuno et al. (1995) and Hanssen (1996) include this mushroom in a group of polypores, the hot water extracts of which provide a strong host mediated response. Agarikon was also applied topically, in a poultice, as an anti-inflammatory and to treat muscle/skeletal pain. Described by the first century Greek physician Dioscorides in *Materia Medica*, the first encyclopedic pharmacopoeia on the medicinal use of plants, in approximately 65 C.E., as a treatment for a wide range of illnesses, most notably consumption, an archaic medical term. It was not until the invention of the microscope did germ-theory suggest that infections were caused by microbes. A resident on the old growth conifers, especially spruce, hemlock, Douglas fir and on Larch, this amazing mushroom produces a chalky cylindrical fruitbody that adds layers of spore-producing pores with each growth season, allowing for a rough calculation of age. Conks up to 50 years have been collected, and often times they resemble a woman, reminiscent of the Venus of Willendorf form. The Haida First Peoples of the Queen Charlotte Islands, and elsewhere on the coast of British Colombia, associated this mushroom, or debatably another polypore species, with the powerful creator spirit Raven, and as a protector of women's sexuality (Blanchette et al., 1992; Stamets, 2002). This mushroom was carved into animalistic forms and placed on shaman's graves to protect them from evil spirits. Grzywnowicz (2001) described the traditional use of this mushroom by Polish peoples, as a treatment against coughing illnesses, asthma, rheumatoid arthritis, bleeding, infected wounds, and was known for centuries as a "elixirium ad longam vitam": elixir of long life. The North Coast First Peoples of Northwestern North America also discovered the use of this mushroom as a poultice to relieve swellings and in teas for treating feverish illnesses. Called the Quinine Fungus in many forestry manuals because of its bitter taste, this mushroom is not the source of quinine, an alkaloid from the bark of the Amazonian *Cinchona ledgeriana* tree which was widely used since the late $19^{th}$ century to treat malaria, caused by *Plasmodium falciparum*. Despite the long history of use, few modern studies have been published on its medicinally active compounds. *F. officinalis* merits further research as the number of strains is in rapid decline, especially in Europe, where it is on the verge of extinction (Leck, 1991).

The present inventor incorrectly speculated that it is thought, but not yet proven, that *Fomitopsis officinalis* provided an aid in preventing the scourge of viral diseases such as smallpox among native populations of northwestern North America (Stamets 2002). Upon further investigation, the inventor contacted Guujaaw (2004), President of the Haida People who told him "We did not have time to develop a defense against smallpox. Our people went from 50,000 to 500 in three years. The smallpox came from a passenger dropped from the ship, the Queen Charlotte. Had we known of a cure, we would have used it." Moreover, tests of the hot-water extract from boiling this mushroom showed no antiviral activity with the U.S. Defense Department's Bioshield BioDefense Program whilst the water/ethanol extract from the in vitro grown mycelium originating from a tissue clone of this mushroom showed strong anti-pox virus activity (U.S. patent application Ser. No. 11/029,861).

*Piptoporus betulinus* (Bull.:Fr.) Karst (=*Polyporus betulinus* (Bull.:Fr.) Fr.) is commonly known as the Birch Polypore or Kanbatake. It is found throughout the birch forests of the world, circumboreal, and is one of the most common mushrooms on that host. Known constituents include betulin, betulinic acid, agaric acid, single stranded RNA, heteroglucans, and antibiotics. Forms used include mushrooms, mycelium on grain and fermented mycelium. Crude extracts and purified fraction are tumor inhibiting in vitro. The novel antibiotic, Piptamine, has been isolated from this fungus (Schlegel et al. 2000). Pisha et al. (1995) found, in mice studies, that betulinic acid, a pentacyclic triterpene, was specifically toxic to melanoma without adverse effects to the host. Farnsworth et al. (1995) found that betulinic acid facilitated apoptosis of melanoma. This compound has been further evaluated for the treatment or prevention of malignant melanoma. Manez et al. (1997) found that selected triterpenoids reduced chronic dermal inflammation. Found with the famous Ice Man, the use of *P. betulinus* transcends cultures and millennia. A fungus useful to stop bleeding, prevent bacterial infection, and as an antimicrobial agent against intestinal parasites, this species is one of the most prominent and frequently encountered mushroom seen on birch. Capasso (1998) postulated that the Ice Man used this fungus to treat infection from intestinal parasites (*Trichuris trichiura*).

Summaries of the antiviral properties of mushrooms were published by Suay et al. (2000), Brandt & Piraino (2000) and Stamets (2001, 2002). Besides having a direct antiviral or antimicrobial effect, mushroom derivatives can also activate natural immune response, potentiating host defense, and in effect have an indirect but significant activity against infections. (Stamets, 2003).

As mushrooms share a more common evolutionary history with animals than with any other kingdom, mushrooms and humans suffer from common pathogens in the microbial world, for instance, the bacterium *Staphylococcus aureus* and *Pseudomonas flourescens*. Mushrooms have a vested evolutionary interest in not being rotted by bacteria, producing antibacterial agents to stave off infection. Work by Suay et al. (2000) showed that various mushroom species have antibacterially specific properties. Viral infections, as in viral pneumonia, can precede, for instance, bacterial infections from *Streptococcus pneumoniae* or *Staphylococcus aureus*, so the use of mushrooms having antibacterial properties can help forestall secondary infections from opportunistic pathogens. Mushrooms having both antibacterial and antiviral properties are especially useful for preventing infection. Furthermore, it is anticipated that some mushrooms will demonstrate anti-bacteriophagic properties, being dually antibacterial and antiviral.

Mushrooms have within them polysaccharides, glycoproteins, ergosterols, enzymes, acids and antibiotics, which individually and in concert can mitigate viral infection. As each species of mushrooms is unique, not only in its cellular architecture, but also in its innate response to viral antagonists, animals, especially humans, can benefit from these antiviral mushroom-derived agents. Since humans now face multiple threats from numerous viruses, including but not limited to HIV, Pox (such as small pox), West Nile virus, influenza and avian or bird flu viruses, coronaviruses such as SARS, hepatitis, Lyme disease, HELA cervical virus, respiratory syncytial virus, hantavirus, vesicular stomatitus, Herpes, Epstein Barr, Varicella-Zoster, Polio, Yellow Fever, Marburg, Ebola, VEE, Lassa and Dengue Fever, and numerous microbes including *Plasmodium falciparum, Bacillus anthracis, Escherichia coli*, anthrax, *Mycobacterium tuberculosis*, bacteriophages, fungi such as *Candida albicans, Aspergillus, Fusarium, Stachybotrys* and *Thernoactinomycetes*, as well as prions such as BSE, finding substances that afford a broad shield of protection against multiple viruses and microbes is difficult. Virologists are increasingly concerned about the threat of viral infection from animal hosts, thought to be the probable source of the 2003 SARS (Sudden Acute Respiratory Syndrome) epidemic, likely to have originated in rural regions of China where humans and captured animals exist in close quarters. Furthermore, the concentration of animals in 'factory farms' wherein thousands of chickens, hogs, cows and other animals are aggregated, provide a breeding environment for contagions as well as other environmental catastrophes. Viruses and bacteria can also breed when birds, dogs, prairie dogs, vermin, cats, primates, bats and other animals, including humans, have concentrated populations. These sources, and more yet to be discovered, present a microbial threat to human health.

Smallpox is a serious acute, contagious and infectious disease marked by fever and a distinctive progressive skin rash. The majority of patients with smallpox recover, but death may occur in up to 30% of cases. Many smallpox survivors have permanent scars over large areas of their body, especially their face, and some are left blind. Occasional outbreaks of smallpox have occurred for thousands of years in India, western Asia and China. European colonization in both the Americas and Africa was associated with extensive epidemics of smallpox among native populations in the 1500s and 1600s, including use as a potential biological weapon in the United States. Smallpox was produced as a weapon by several nations well past the 1972 Bioweapons convention that prohibited such actions.

There is no specific treatment for smallpox and the only prevention is vaccination. In 1980, the disease was declared eradicated following worldwide vaccination programs. However, in the aftermath of the terrorist and anthrax attacks of 2001, the deliberate release of the smallpox virus is now regarded as a possibility and the United States is taking precautions to deal with this possibility.

Smallpox is classified as a Category A agent by the Centers for Disease Control and Prevention. Category A agents are believed to pose the greatest potential threat for adverse public health impact and have a moderate to high potential for large-scale dissemination. Other Category A agents are anthrax, plague, botulism, tularemia, and viral hemorrhagic fevers. Even the remote potential for release of a deadly communicable disease in an essentially non-immune population is truly frightening.

Orthopox (Orthopoxvirus) includes the virus that causes smallpox (Variola major). Smallpox infects only humans in nature, although other primates have been infected in the laboratory. Other members of the Orthopoxvirus genera capable of infecting humans include monkeypox, camelpox, cowpox, and vaccinia. Other poxviruses capable of infecting humans include the Parapoxvirus pseudocowpox and Orf (Parapoxvirus ovis) and the Molluscipoxvirus *Molluscum contagiosum*. Monkeypox is a rare smallpox-like disease encountered in villages in central and west Africa. It is transmitted by monkeys, primates and rodents. Camelpox is a serious disease of camels. The genetic sequence of the camelpox virus genome is most closely related to that of the Variola (smallpox) virus. Cowpox is usually contracted by milking infected cows and causes ulcerating "milker's nodules" on the hands of dairy workers. Cowpox protects against smallpox and was first used for vaccination against smallpox. Pseudocowpox is primarily a disease of cattle. In humans it causes non-ulcerating "milker's nodes." *Molluscum contagiosum* causes minor warty bumps on the skin. It is transferred by direct contact, sometimes as a venereal disease. Orf virus occurs worldwide and is associated with handling sheep and goats afflicted with "scabby mouth." In humans it causes a single painless lesion on the hand, forearm or face. Vaccinia, a related Orthopox of uncertain origin, has replaced cowpox for vaccination. Other viruses of the Poxyiridae family include buffalopox virus, rabbitpox virus, avipox virus, sheep-pox virus, goatpox virus, lumpy skin disease (Neethling) virus, swinepox virus and Yaba monkey virus.

Poxviruses are very large rectangular viruses the size of small bacteria. They have a complex internal structure with a large double-stranded DNA genome enclosed within a "core" that is flanked by two "lateral bodies." The surface of the virus particle is covered with filamentous protein components, giving the particles the appearance of a ball of knitting wool. The entire virus particle is encapsulated in an envelope derived from the host cell membranes, thereby "disguising" the virus immunologically. Most poxviruses are host-species specific, but Vaccinia is a remarkable exception. True pox viruses are antigenically rather similar, so that infection by one elicits immune protection against the others.

Influenza ("flu") is an infection of the respiratory system characterized by fever, body aches, chills, dry cough, headache, sore throat and stuffy nose. The flu, which is caused by a variety of viruses, is notable for its ability to sweep through entire communities in both developed and developing countries and is associated with high morbidity and a significant death rate. Half the population of a community may be affected during an epidemic. Children are much more likely than adults to get sick from the flu, as are families with school-age children—schools are an excellent place for flu viruses to infect and spread. The risk of death from influenza is highest among persons aged 65 or older, although young children, particularly the newborn, and persons with certain chronic conditions are also at risk of death. The flu is particularly serious because of the rapidity of outbreaks, the large number of people affected and the possibility of serious complications such as pneumonia. The Centers for Disease Control and Prevention estimates that 5-20% of the population of the United States come down with the flu each flu season (typically late fall through winter). Although most recover from the illness, according to CDC estimates about 19,000-36,000 died from the flu and its complications each year during the epidemics occurring from 1976-1999. The 1918 Spanish flu pandemic is estimated to have caused 20-40 million deaths worldwide, including 500,00 in the United States. The majority of the 1918 deaths were caused by secondary infections from bacteria, which exploited the scarred lung tissue and immune impairment. The 1957 Asian flu and the 1968 Hong Kong flu outbreaks killed hundreds of thousands in the United States.

The influenza viruses are RNA viruses belonging to the Orthomyxoviridae family. Influenza viruses are classified into types A, B and C. Type A is the most common and usually causes the most serious epidemics. Influenza A viruses are further divided into subtypes on the basis of two proteins found on the surface of the virus, hemagglutinin (H) and neuraminidase (N). Influenza A viruses are found in many different animals, including birds, pigs, whales and seals, with wild birds acting as the reservoir for all subtypes of influenza A viruses. The influenza A subtypes H1N1 and H3N2 have circulated widely among people (the Spanish flu was a H1N1 virus and the Hong Kong flu was a H3N2 virus). Type B can also cause epidemics, but generally produces a milder disease than that caused by type A. Type C viruses have never been connected with major epidemics. Yearly flu vaccines are available targeting new variant strains resulting from antigenic drift, but neither prior vaccination nor previous infection guarantees protection from the flu since the virus typically varies from year to year.

It is currently feared that a strain of avian influenza ("bird flu"), which naturally occurs in wild birds and can spread to domesticated birds, could mutate into a form easily transmissible by human-to-human and cause a worldwide pandemic. The H5N1 high pathogenicity avian influenza (HPAI) virus strain, which is becoming endemic in various Asian countries and has spread to a number of countries in the Middle East, Africa and Europe, has particularly concerned researchers because it is spread by migratory wildfowl, because it is especially virulent and has caused the death of millions of animals worldwide, because it mutates rapidly and continues to evolve and because it has spread to domesticated birds and mammals including pigs and tigers and in limited circumstances to humans. As influenza type A H5 hemagglutinin viruses have not circulated among humans and most or all of the population has no protective antibodies, there is the potential that H5N1 could cause a pandemic were it to mutate to a form easily transmissible by human-to-human contact. The H5N1 avian influenza strain has caused illness in more than several hundred people in Asia and the Middle East, approximately half of whom have died (almost all cases are thought to be the result of bird-to-human infection, but it appears there may be rare cases of human-to-human transmission). A severe influenza pandemic could potentially result in unprecedented death, social disruption and economic loss as millions become seriously ill at the same time.

SARS is a new viral illness spread mainly by close person-to-person contact and possibly by infected surfaces or objects or an airborne vector or other means. SARS is believed to have originated in rural China in November 2002. In March 2003 the alarming spread of cases caused the World Health Organization and U.S. Centers for Disease Control and Prevention to issue a global alert over cases of atypical pneumonia that did not appear to respond to treatment. The illness was named Severe Acute Respiratory Syndrome (SARS). By the third week of March 2003, researchers from several countries had isolated a novel single-stranded RNA virus from the Coronavirus family (SARS-CoV) with contagiousness and high mortality rate unlike any other known human coronaviruses. Although coronaviruses account for about thirty percent of respiratory illnesses, most are moderate in course (such as common colds) with pneumonia being caused only in patients with poor immune systems; SARS-CoV seemed to be the first Coronavirus that consistently caused severe disease in humans. Before the outbreak was contained, it spread to more than two dozen countries. By December of 2003, 774 people had died and more than 8,000 had been infected. World airlines were hit hard by the SARS epidemic as several carriers slashed flights and axed jobs. The tourism industry suffered badly due to the fear unleashed by the outbreak, as did many other businesses and industries far from its epicenter. In many ways SARS caused the worst economic crisis in Southeast Asia since the wave of bank failures and currency devaluations that occurred there in 1988.

SARS causes a form of lung injury characterized by increased permeability of the alveolar-capillary membrane, diffuse alveolar damage, the accumulation of proteinaceous pulmonary edema and pulmonary failure. Symptoms included high fever and one or more respiratory symptoms including, cough, shortness of breath and difficulty breathing. In addition to fever and respiratory symptoms, SARS was associated with other symptoms including headache, muscular stiffness, loss of appetite, malaise, confusion, rash, diarrhea and low oxygen levels in the blood (hypoxia). In many cases, those symptoms were followed by pneumonia in both lungs, sometimes requiring use of a respirator. The pathology of SARS is not yet fully understood and the clinical symptoms are unusual. The disease was mild in children and the mortality rate in that group almost nonexistent. Persons who suffered from chronic disease and the elderly had a much higher mortality rate. Patients who survived SARS infections recovered seemingly spontaneously while those who perished succumbed to rapid respiratory decline accompanied by extensive lung tissue damage. The tissue damage appeared to be driven by the patient's own immune system rather than the organism itself. The mechanism of SARS pathogenesis may involve both direct viral cytocidal effects on the target cells and immune-mediated mechanisms. There are no specific therapies for SARS. The use of physiologically targeted strategies of mechanical ventilation and intensive care unit management including fluid management and glucorticoids was the only supportive therapy available. Numerous antibiotic therapies were tried with no clear effect. Ribavirin with or without use of steroids was used in a number of patients. But, in the absence of clinical indicators, its effectiveness was not proven.

SARS was a much more virulent strain than most coronaviruses, leading scientists to believe that the virus had its origins in a non-human animal, where a coronavirus can have more severe effects. Although this virus most likely originated from a wild animal, perhaps the civet cat, the SARS virus was well adapted in humans as evidenced by the high person-to-person transmissibility of the virus. The critical questions are whether there is extensive horizontal transmission between animals, and whether the jump of the virus from animals to human was a rare and accidental event or portends frequent occurrences in the future. The answers to these questions will determine whether animals are viable reservoirs for future SARS outbreaks and whether person-to-person transmission of SARS-CoV might recur.

With the flow of airline passengers from remote regions of the world, concentrating in airports and being re-routed to their destinations, the contagiousness of foreign-borne viruses carried by passengers are likely to be exacerbated in these types of locations, especially within the closed compartments of passenger airplanes, increasing the likelihood of cross-infection. Virtually anywhere humans concentrate provide opportunities for contagions to spread, whether by air or by physical contact. The history of viruses indicates the danger posed by new strains for which no immunities or vaccines exist. With the increased threat of bioterrorism from weaponized viruses, a readily available broad-spectrum antiviral serves the best interests of public health.

BRIEF SUMMARY OF THE INVENTION

Medicinal mushrooms having unique antiviral and antibacterial properties are described, including mushroom species, mycelium, extracts and derivatives useful in preventing, treating ameliorating, mitigating, alleviating, reducing or curing infection from viruses. Particularly preferred are *Fomitopsis, Piptoporus, Inonotus, Ganoderma, Hypsizygus, Trametes* and various combinations with other mushroom species. Extracts showing target specific antiviral and antibacterial properties are disclosed, as well as methods for preparation and isolation of active fractions.

Still further objects and advantages of this invention will become more apparent from the following detailed description and appended claims. Before explaining the disclosed embodiments of the present invention in detail, it is to be understood that the invention is not limited in its application to the details of the particular products and methods illustrated, since the invention is capable of other embodiments which will be readily apparent to those skilled in the art. Also, the terminology used herein is for the purpose of description and not of limitation.

BRIEF DESCRIPTION OF THE DRAWING(S)

DETAILED DESCRIPTION OF THE INVENTION

Figure 1:
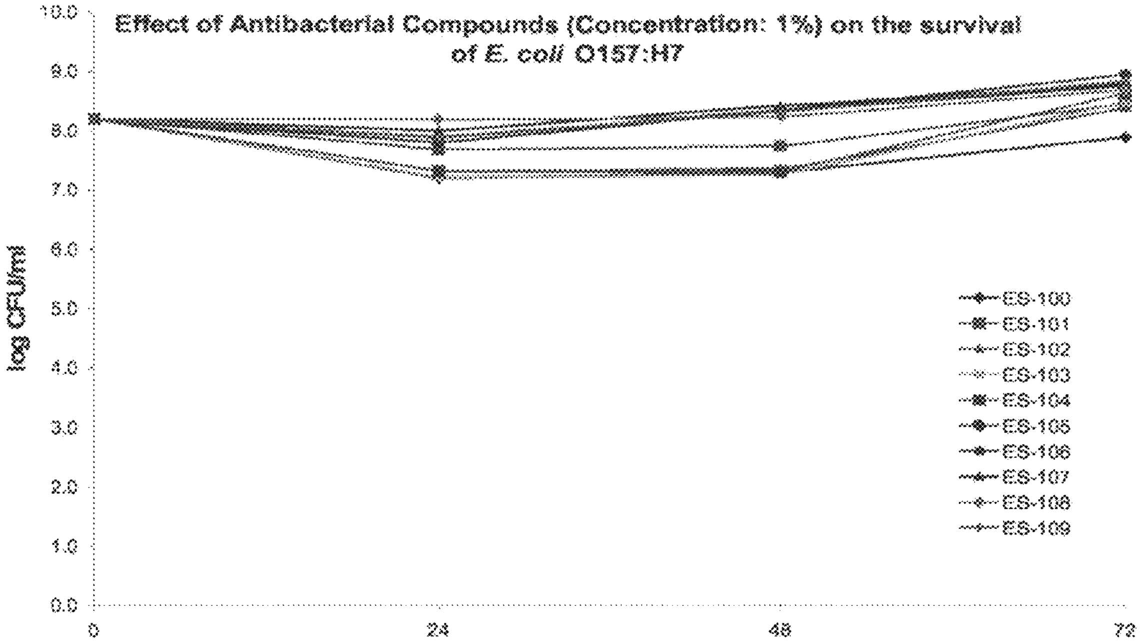
FIG. 1 is a chart showing the effect of antibacterial compounds (concentration: 1%) on the survival of *E. coli* (*Escherichia coli*) O157:H7.

The extracts of the mushroom mycelium of *Fomitopsis officinalis, Fomitopsis pinicola, Piptoporus betulinus, Ganoderma resinaceum, Inonotus obliquus, Hypsizygus ulmarius* and various combinations of other species have been found by the present inventor to have unique antiviral properties, including activity against Orthopox viruses.

Orthopox viruses have a notorious reputation for their surviving outside of the carrier-host animal, surviving on surfaces such as blankets, on dead skin cells, and can be readily transmitted through bodily fluids, whether they are aspirated or not. That these viruses can survive long after their host cells have died makes orthopoxes especially capable of widespread distribution. Novel antiviral agents are needed to reduce the survivability of viruses beyond that of disinfectants currently in practice. Moreover, since the entry of viruses are commonly through the nasal and throat cavities, or through sexual contact, contact antivirals that limit the survivability of the virus, or kill the virus, and/or limit the susceptibility of human cells to infection by a pox virus while selectively not harming healthy human cells, are needed. Such contact antivirals as disclosed herein could prove useful in many applications, closing some of the many vectors used by this virus for transmission to new hosts.

Rather than the mushrooms themselves, particularly preferred is the live mushroom mycelium (the "vegetative" state of the mushroom, containing at most only primordia or young mushrooms) and extracts thereof, particularly the cell free (centrifuged) extracts. The mycelium may be cultivated, grown or fermented on solid, semi-solid or liquid media. Preferred derivatives include frozen, dried or freeze-dried mycelium, extracts thereof and dried, solvent-free extracts (including both "crude" extracts and cell-free centrifuged extracts). It was unexpectedly found that boiling of the mushroom in water created water extracts that showed no activity against pox viruses whereas the mycelium grown from a clone of the same mushroom did.

Preferred antiviral species include the *Fomitopsis* species, particularly *F. officinalis* and *F. pinicola; Piptoporus* species, particularly *P. betulinus; Ganoderma* species, particularly *Ganoderma annulare* (*G. annularius*), *G. lucidum, G. resinaceum*, and *G. camosum; Hericium* species, particularly *H. erinaceus; Hypsizygus* species, particularly, *H. tessulatus* and *H. ulmarius; Inonotus* species, particularly *I. obliquus; Trametes* species, particularly *Trametes versicolor* and the constellations of species complexes derived from them throughout the evolution of taxonomic and nomenclatural history.

*Fomitopsis* species include *F. africana, F. albomarginata* var. *pallida, F. albomarginata* var. *polita, F. albomarginata* var. *subvillosa, F. anhuiensis, F. annosa f. multistriata, F. annosa* var. *indica, F. arbitraria, F. avellanea, F. bucholtzii, F. cajanderi, F. caliginosa, F. castanea, F. cinerea, F. concava, F. connata, F. corrugata, F. cuneata, F. cupreorosea, F. cystina, F. cytisina, F. dochmia, F. durescens, F. epileucina, F. euosma, F. feei, F. fulviseda, F. hainaniana, F. iberica, F. ibericus, F. kiyosumiensis, F. komatsuzakii, F. labyrinthica, F. latissima, F. lignea, F. lilacinogilva, F. maackiae, F. maire, F. marginata, F. mellea, F. minutispora, F. nigrescens, F. nivosa, F. odoratissima, F. officinalis* (=*Laricifomes officinalis*), *F. olivacea, F. palustris, F. pinicola, F. pinicola f. effusa, F. pinicola f. paludosa, F. pinicola f. resupinata, F. pseudopetchiin, F. pubertatis, F. quadrans, F. rhodophaea, F. rosea, F. roseozonata, F. rubidus, F. rufolaccata, F. rufopallida, F. sanmingensis, F. scalaris, F. semilaccata, F. sensitiva, F. spraguei, F. stellae, F. subrosea, F. subungulata, F. sulcata, F. sulcata, F. supina, F. unita, F. unita* var. *lateritia, F. unita* var. *multistratosa, F. unita* var. *prunicola, F. vinosa, F. widdringtoniae, F. zonalis* and *F. zuluensis* and *Laricifomes* species including *L. concavus, L. maire* and *L. officinalis. Piptoporus* species include *P. betulinus, P. choseniae, P. elatinus, P. fraxineus, P. helveolus, P. maculatissimus, P. malesianus, P. paradoxus, P. quercinus f. monstrosa, P. soloniensis, P. suberosus* and *P. ulmi.*

The mycelial products of the present invention are preferably grown on grains; rice is very suitable. The mycelium may alternatively be grown on various agricultural and forestry products, by-products and waste products or synthetic media and the antiviral metabolites and products harvested using methods known to the art. Alternatively, the mycelium may be grown via liquid fermentation and the antiviral products harvested subsequent to colonization. The methods for cultivation of mycelium that are contemplated are covered within, for example, but are not limited to, the techniques described by Stamets (1993, 2000) in *Growing Gourmet and Medicinal Mushrooms*, and by Stamets (2005) in *Mycelium Running: How Mushrooms Can Help Save the World.*

Although ethanol and water extracts are illustrated below, it will be obvious that the various solvents and extraction methods known to the art may be utilized. The extracts may optionally be prepared by methods including extraction with water, alcohols, organic solvents and supercritical fluids such as $CO_2$, etc. Extracts may also be prepared via steam distillation of volatile components, similar to the preparation of "essential oils" from flowers and herbs. Suitable alcohols include those containing from 1 to 10 carbon atoms, such as, for example, methanol, ethanol, isopropanol, n-propanol, n-butanol, 2-butanol, 2-methyl-1-propanol (t-butanol), ethylene glycol, glycerol, etc. Suitable organic solvents include unsubstituted organic solvents containing from 1 to 16 carbon atoms such as alkanes containing from 1 to 16 carbon atoms, alkenes containing from 2 to 16 carbon atoms, alkynes containing from 2 to 16 carbon atoms and aromatic compounds containing from 5 to 14 carbon atoms, for example, benzene, cyclohexane, cyclopentane, methylcyclohexane, pentanes, hexanes, heptanes, 2,2,4-trimethylpentane, toluene, xylenes, etc., ketones containing from 3 to 13 carbon atoms such as, for example, acetone, 2-butanone, 3-pentanone, 4-methyl-2-pentanone, etc., ethers containing from 2 to 15 carbon atoms such as t-butyl methyl ether, 1,4-dioxane, diethyl ether, tetrahydrofuran, etc., esters containing from 2 to 18 carbon atoms such as, for example, methyl formate, ethyl acetate and butyl acetate, nitriles containing from 2 to 12 carbon atoms such as, for example acetonitrile, proprionitrile, benzonitrile, etc., amides containing from 1 to 15 carbon atoms such as, for example, formamide, N,N-dimethylformamide, N,N-dimethylacetamide, amines and nitrogen-containing heterocycles containing from 1 to 10 carbon atoms such as pyrrolidine, 1-methyl-2-pyrrolidinone, pyridine, etc., halogen substituted organic solvents containing from 1 to 14 carbon atoms such as, for example, bromotrichloromethane, carbon tetrachloride, chlorobenzene, chloroform, 1,2-dichloroethane, dichloromethane, 1-chlorobutane, trichloroethylene, tetrachloroethylene, 1,2-dichlorobenzene, 1,2,4-trichlorobenzene, 1,1,2-trichlorotrifluoroethane, etc., alkoxy, aryloxy, cyloalkyl, aryl, alkaryl and aralkyl substituted organic solvents containing from 3 to 13 carbon atoms such as, for example, 2-butoxyethanol, 2-ethoxyethanol, ethylene glycol dimethyl ether, 2-methoxyethanol, 2-methoxyethyl ether, 2-ethoxyethyl ether, etc., acids containing from 1 to 10 carbon atoms such as acetic acid, trifluoroacetic acid, etc., carbon disulfide, dimethyl sulfoxide (DMSO), nitromethane and combinations thereof. Extracts may also be prepared via sequential extraction with any combination of the above solvents. The extracts may be further refined by means known to the art.

Preferred drying methods include freeze drying, air drying, spray drying and drum drying and the methods and apparatus for drying mycelium, extracellular metabolites, extracts and derivatives disclosed in U.S. Pat. No. 4,631,837 to Magoon (1986), herein incorporated by reference in its entirety. Extracts are preferably extracted from living mycelium and may be cell-free (filtered and/or centrifuged) or not.

The products from the culturing of the medicinal mushroom species and mycelia, extracts and derivatives can be deployed via several delivery systems as an effective antiviral control, including orally-active powders, pills, capsules, teas, extracts, dried extracts, sublinguals, sprays, dispersions, solutions, suspensions, emulsions, foams, syrups, lotions, ointments, gels, pastes, dermal patches, injectables, vaginal creams and suppositories.

The mycelium, extracts and derivatives of *Fomitopsis officinalis, Piptoporus betulinus* and/or *Ganoderma resinaceum* may optionally be combined with *Agaricus blazei, Agaricus brasiliensis, Agrocybe arvalis, Agrocybe aegerita, Auricularia auricula, Auricularia polytricha, Calvatia gigantean, Cordyceps sinensis, Flammulina populicola, Flammulina velutipes, Fomes fomentarius, Fomitopsis cajanderi, Fomitopsis pinicola, Ganoderma applanatum, Ganoderma capense, Ganoderma lucidum, Ganoderma oregonense, Ganoderma sinense, Ganoderma neojaponicum, Ganoderma tsugae, Giganopanus giganteum, Grifolafrondosa, Hericium abietis, Hericium erinaceus, Hericium ramosum, Hypholoma capnoides, Hypholoma sublateritium, Hypsizygus tessulatus, Hypsizygus ulmarius, Inonotus obliquus, Inonotus dryadeus, Inonotus dryophilus, Lentinula edodes, Lentinus ponderosus, Lenzites betulina, Mycena alcalina, Phellinus linteus, Pholiota adipose, Pholiota nameko, Pleurotus citrinopileatus, Pleurotus comucopiae, Pleurotus dryinus, Pleurotus eryngii, Pleurotus ostreatus, Pleurotus opuntinae, Pleurotus pulmonarius, Pleurotus tuberregium, Polyporus sulphureus* (*Laetiporus sulphureus*), *Laetiporus conifericola, Polyporus hirtus, Polyporus tuberaster, Polyporus umbellatus*, (=*Grifola umbellata*), *Schizophyllum commune, Trametes versicolor* (=*Coriolus versicolor*), and/or *Wolfiporia cocos* (=*Poria cocos*) mycelium, extracts or derivatives.

*Fomitopsis* species such as *Fomitopsis officinalis, Piptoporus* species such as *Piptoporus betulinus, Ganoderma* species such as *Ganoderma resinaceum, Inonotus* species such as *Inonotus obliquus*, and *Trametes* species, such as *Trametes versicolor*, may optionally be added to any formula or product in an amount sufficient to have the effect of preventing, treating, alleviating, mitigating, ameliorating or reducing infection.

The invention includes the combination of products from multiple mushroom species in a form to have the accumulated effect of restricting the growth, spread and survivability of viruses in animals, especially humans. Such forms may have the additional advantages of functioning as antibacterials, antiprotozoals, immunomodulators, nutraceuticals and/or probiotics as well as enhancing innate immunity defense mechanisms and host immune response, resulting in healing.

Optimizing dosage is dependent upon numerous variables. The difference between a medicine and poison is often dosage. Determining the proper dose for antiviral effects will only require routine experimentation because the concentrations of extracts can be simply diluted or concentrated by adjusting ethanol and/or water content. In general, with regard to *Fomitopsis officinalis* blends, blends consisting of 5-95% F.o. are preferred, 10-75% is more preferred and 20-50% is most preferred.

The term "effective amount" refers to an amount sufficient to have antiviral activity and/or enhance a host defense mechanism as more fully described below. This amount may vary to some degree depending on the mode of administration, but will be in the same general range. The exact effective amount necessary could vary from subject to subject, depending on the species, preventative treatment or condition being treated, the mode of administration, etc. The appropriate effective amount may be determined by one of ordinary skill in the art using only routine experimentation or prior knowledge in the art in view of the present disclosure. Typical therapeutic amounts of mycelium on rice (individual fungal species and/or combinations of species) are preferably 0.1-20 gm./day, more preferably 0.25-10 gm./day, and most preferably 0.5-5 gm./day. Typical therapeutic amounts of extracts (individual fungal species and/or combinations of species) preferably deliver 0.1-20 mg. extracted materials per kg. of body weight, more preferably 0.25-10 mg./kg. and most preferably 0.5-5 mg./kg.

The antiviral extracts, mycelium and/or other derivatives may be incorporated into foods to produce foods with antiviral properties, useful for protecting animals, including humans, dogs cats, horses, cows, pigs, birds, fish, insects and other wild and domesticated animals, from infection.

The applicant anticipates that since DNA techniques and other advances in taxonomy will likely result in changes in names, the splitting of species, and even in the transfer of species to other genera, that the Polyporaceae species mentioned in this patent application are those as understood by the most complete monograph on the subject, Ryvarden & Gilbertson's *North American Polypores,* 1986 vol. I and II, FungiFlora, Oslo, Norway. As such, when we describe *Fomitopsis officinalis, Piptoporus betulinus* or any other mushroom species, we mean *Fomitopsis officinalis* sensu lato, *Piptoporus betulinus* sensu lato and a similar broad description of any other species, each of which means that this is the species concept as described within the broadest taxonomic interpretation, encompassing synonyms, varieties, forms and species that have or will be split from these species since original publication. As is known in the art, names change as new species concepts are constructed.

Example 1

Tissue cultures of the mushrooms species describe herein were acquired or cloned from wild specimens by the inventor and purified over time by successive transfers in a clean room laboratory using standard tissue culture techniques as described in *Growing Gourmet and Medicinal Mushrooms* Stamets (1993, 2000). *Fomitopsis officinalis* I is a strain collected from Morton, Wash., USA. *Fomitopsis officinalis* X is a strain isolated from the Hoh Rainforest, Wash., USA. Other species were either collected or obtained from culture banks. The *Ganoderma resinaceum* utilized is a strain formerly misidentified as *G. lucidum*. Phylogenetic analysis of *Ganoderma* based on nearly complete mitochondrial small-subunit ribosomal DNA sequences, Soon Gyu Hong and Hack Sung Jung, *Mycologia,* 96(4), 2004, pp. 742-745.

Mycelial cultures were grown in sterile Petri dishes containing sterilized malt yeast rice agar. After three weeks of colonization in a clean room laboratory, the cultures were aseptically transferred into a 1000 ml. EBERBACH™ stirrer containing 800 ml. of sterilized water. The EBERBACH™ container was activated using a WARING™ blender base, chopping the mycelium into thousands of fragments. This myceliated broth was then transferred, under sterile conditions, into a sterilized glass 2000 ml. fermentation vessel containing a 3% concentration of malt sugar, 0.3% yeast and 0.3% powdered rice, stir bar and 800 ml. of sterilized water. Once transferred, the fermentation flask was placed on a magnetic stir plate, and stirred at 300-400 rpm for a period of 3-4 days in front of a laminar flow hood at a temperature of 70°-75° F. During that time, three-dimensional colonies of mycelium appeared, increasing in numbers and in density. The fermentation was stopped prior to the coalescing of the mycelium into a contiguous mycelial mat. The dissociated fragmented mycelial mass allows for a multiple loci inoculation, resulting in accelerated colonization and allowing for the ease of further dilutions and inoculations. The fermented broth was then diluted 1:10 into sterilized water, and transferred, under sterile conditions, into polypropylene incubation bags containing approximately 6.6 lbs or 3 kg. moistened sterilized rice, adjusted to approximately 45-50% moisture content. Approximately 50-100 ml. of diluted fermented fluid was transferred into each of the 10 rice bags under sterile conditions. The fresh mycelial cultures were then incubated for 60-120 days in a class 100 clean room. Incubation times are preferably 7-180 days, more preferably 30-120 days.

Once colonization was determined to be sufficient, the mycelium-colonized rice was transferred to glass containers for extraction. The mycelium, being delicate in nature, was handled with utmost gentle care so as to not to cause cell damage in transfer and immediately covered with an approximately equal weight of 50% ethanol-water (prepared by mixing equal weights of 95% (190 proof) organic ethyl alcohol and spring water), agitated, and then allowed to rest for room temperature infusion-extraction for a total of 14 days. Cultures of *Fomitopsis officinalis, Piptoporus betulinus, Ganoderma resinaceum* and the various other species were treated separately in a similar fashion to the methods described herein. The clear fluid, the supernatant, was drawn off and decanted into 2 ounce amber bottles or other containers. Dilution for bioassay was from 1:100 to 1:1000.

It will of course be appreciated that differing concentrations and/or compositions of extracts may be easily prepared; 3 kg. of fresh mycelium on rice for every 3000 ml. of extract. or 1 g. mycelium/1 ml. extract is an example of a therapeutically useful extract.

Example 2

Proprietary strains of fungal species, sourced and/or originated by Stamets and Fungi Perfecti LLC, were grown under Class 100 clean room conditions on sterilized, certified organic short grain brown rice, in accordance to methods described by Stamets (1993, 2000) in *Growing Gourmet and Medicinal Mushrooms*. The moistened rice was sterilized in high-density polypropylene bags and inoculated with mycelium, which was fermented in liquid culture for several days. Each strain was grown to optimize the number of cell divisions (CFU's=colony forming units) prior to transfer into grain. Once inoculated, each strain was incubated for a duration to optimize their CFU (colony forming units) maxima, and then flash frozen to −18° C. The frozen myceliated rice was then freeze-dried in a negative pressure vacuum of 1500-2000 millibars and then heated to 75° C. for 24 hours. The freeze-dried material was then milled to a fineness of 20-80 standard mesh (180-850 microns). This raw material can be filled into capsules, made into tablets, tinctures or further used as a base for a medicinal product effective as a antimicrobial and/or for potentiating a host mediated response. Products made from *Fomitopsis officinalis, Fomitopsis pinicola* and *Piptoporus betulinus* may be combined with other mushrooms, fungi, or plant based materials to positive affect immunity, host defense and resistance from infectious diseases. Grains other than rice may be additionally employed with similarly positive results.

Example 3

The general approach for determining antiviral activity and toxicity as described by E. Kern for orthopoxviruses (http://www.niaid-aacf.org/protocols/orthopox.htm) was utilized. The Selectivity Index (SI) values were determined by or under the direction of Dr. Earl Kern of the USAMRIID/NIH/USAID Bioshield BioDefense Program.

An inexpensive, rapid assay such as a CPE-inhibition assay that is semi-automated was used initially to screen out the negatives. Screening assays were conducted in low-passaged human cells. Each assay system contained a positive control (CDV) and a negative control (ACV). Toxicity was determined using both resting and proliferating human fibroblast cells.

Screening Assay Systems for Determining Antiviral Activity Against VV and CV

Compounds were screened for activity against Vaccinia virus (VV) and Cowpox virus (CV) using the CPE assay in HFF cells. The screening assay systems utilized were selected to show specific inhibition of a biologic function, i.e., cytopathic effect (CPE) in susceptible human cells. In the CPE-inhibition assay, drug is added 1 hr prior to infection so the assay system will have maximum sensitivity and detect inhibitors of early replicative steps such as adsorption or penetration as well as later events. To rule out non-specific inhibition of virus binding to cells all compounds that show reasonable activity in the CPE assay can be confirmed using a classical plaque reduction assay in which the drug is added 1 hr after infection. These assay systems also can be manipulated by increasing the pre-treatment time in order to demonstrate antiviral activity with oligodeoxynucleotides and/or peptides. By delaying the time of addition of drug after infection, information regarding which step in the virus life cycle is inhibited (i.e., early vs. late functions) can be gained.

Efficacy:

In all the assays used for primary screening, a minimum of six drug concentrations was used covering a range of 100 μg/ml to 0.03 μg/ml, in 5-fold increments. These data allowed good dose response curves. From these data, the dose that inhibited viral replication by 50% (effective concentration 50; $EC_{50}$) was calculated using the computer software program MacSynergy II by M. N. Prichard, K. R. Asaltine, and C. Shipman, Jr., University of Michigan, Ann Arbor, Mich.

Toxicity:

The same drug concentrations used to determine efficacy were also used on uninfected cells in each assay to determine toxicity of each experimental compound. The drug concentration that is cytotoxic to cells as determined by their failure to take up a vital stain, neutral red, (cytotoxic concentration 50; $CC_{50}$) was determined as above. The neutral red uptake assay has been found to be reliable and reproducible and allows quantitation of toxicity based on the number of viable cells rather than cellular metabolic activity. It is important also to determine the toxicity of new compounds on dividing cells at a very early stage of testing. A cell proliferation assay using HFF cells is a very sensitive assay for detecting drug toxicity to dividing cells and the drug concentration that inhibits cell growth by 50% ($IC_{50}$) was calculated as described above. In comparison with four human diploid cell lines and Vero cells, HFF cells are the most sensitive and predictive of toxicity for bone marrow cells.

Assessment of Drug Activity: To determine if each compound has sufficient antiviral activity that exceeds its level of toxicity, a selectivity index (SI) was calculated according to $CC_{50}/EC_{50}$. This index, also referred to as a therapeutic index, was used to determine if a compound warrants further study. Compounds that had an SI of 2 or more are considered active, 10 or greater (≥10) is considered very active.

Laboratory Procedures for Determining Antiviral Efficacy and Toxicity

Preparation of Compounds for In Vitro Testing:

as the Fungal extracts were water, ethanol and DMSO soluble, they were dissolved in tissue culture medium without serum at 1 mg/ml and diluted for use as indicated below in the description of the assay system. Noteworthy is that the extracts from the applicant's living mycelium, diluted from 100:1 to 1,000:1, showed effectiveness against the described viruses at dosages designed for testing pure pharmaceuticals, underscoring that the extracts as presented are potent against viruses.

Screening and Confirmation Assays for VV and CV

Preparation of Human Foreskin Fibroblast (HFF) Cells:

Newborn human foreskins are obtained as soon as possible after circumcision and placed in minimal essential medium (MEM) containing vancomycin, fungizone, penicillin, and gentamicin at the usual concentrations, for 4 hr. The medium is then removed, the foreskin minced into small pieces and washed repeatedly with phosphate buffered saline (PBS) deficient in calcium and magnesium (PD) until red cells are no longer present. The tissue is then trypsinized using trypsin at 0.25% with continuous stirring for 15 min at 37° C. in a $CO_2$ incubator. At the end of each 15-min. period the tissue is allowed to settle to the bottom of the flask. The supernatant containing cells is poured through sterile cheesecloth into a flask containing MEM and 10% fetal bovine serum. The flask containing the medium is kept on ice throughout the trypsinizing procedure. After each addition of cells, the cheesecloth is washed with a small amount of MEM containing serum. Fresh trypsin is added each time to the foreskin pieces and the procedure repeated until all the tissue is digested. The cell-containing medium is then centrifuged at 1000 RPM at 4° C. for 10 min. The supernatant liquid is discarded and the cells resuspended in a small amount of MEM with 10% FBS. The cells are then placed in an appropriate number of 25 $cm^2$ tissue culture flasks. As cells become confluent and need trypsinization, they are expanded into larger flasks. The cells are kept on vancomycin and fungizone to passage four, and maintained on penicillin and gentamicin. Cells are used only through passage 10.

Cytopathic Effect Inhibition Assay:

Low passage HFF cells are seeded into 96 well tissue culture plates 24 hr prior to use at a cell concentration of $2.5\times10^5$ cells per ml in 0.1 ml of MEM supplemented with 10% FBS. The cells are then incubated for 24 hr at 37° C. in a $CO_2$ incubator. After incubation, the medium is removed and 125 μl of experimental drug is added to the first row in triplicate wells, all other wells having 100 μl of MEM containing 2% FBS. The drug in the first row of wells is then diluted serially 1:5 throughout the remaining wells by transferring 25 μl using the BioMek 2000 Laboratory Automation Workstation. After dilution of drug, 100 μl of the appropriate virus concentration is added to each well, excluding cell control wells, which received 100 μl of MEM. The virus concentration utilized is 1000 PFU's per well. The plates are then incubated at 37° C. in a $CO_2$ incubator for 7 days. After the incubation period, media is aspirated and the cells stained with a 0.1% crystal violet in 3% formalin solution for 4 hr. The stain is removed and the plates rinsed using tap water until all excess stain is removed. The plates are allowed to dry for 24 hr and then read on a BioTek Multiplate Autoreader at 620 nm. The $EC_{50}$ values are determined by comparing drug treated and untreated cells using a computer program.

Plague Reduction Assay Using Semi-Solid Overlay:

Two days prior to use, HFF cells are plated into 6 well plates and incubated at 37° C. with 5% $CO_2$ and 90% humidity. On the date of assay, the drug is made up at twice the desired concentration in 2×MEM and then serially diluted 1:5 in 2×MEM using 6 concentrations of drug. The initial starting concentration is usually 200 μg/ml down to 0.06 μg/ml. The virus to be used is diluted in MEM containing 10% FBS to a desired concentration which will give 20-30 plaques per well. The media is then aspirated from the wells and 0.2 ml of virus is added to each well in duplicate with 0.2 ml of media being added to drug toxicity wells. The plates are then incubated for 1 hr with shaking every 15 min. After the incubation period, an equal amount of 1% agarose will be added to an equal volume of each drug dilution. This gives final drug concentrations beginning with 100 μg/ml and ending with 0.03 μg/ml and a final agarose overlay concentration of 0.5%. The drug/agarose mixture is applied to each well in 2 ml volume and the plates are incubated for 3 days, after which the cells are stained with a 0.01% solution of neutral red in phosphate buffered saline. After a 5-6 hr incubation period, the stain is aspirated, and plaques counted using a stereomicroscope at 10× magnification.

Screening and Confirmation Assays for Toxicity

Neutral Red Uptake Assay

Twenty-four h prior to assay, HFF cells are plated into 96 well plates at a concentration of $2.5\times10^4$ cells per well. After 24 hr, the media is aspirated and 125 μl of drug is added to the first row of wells and then diluted serially 1:5 using the BioMek 2000 Laboratory Automation Workstation in a manner similar to that used in the CPE assay. After drug addition, the plates are incubated for 7 days in a $CO_2$ incubator at 37 C. At this time the media/drug is aspirated and 2001/well of 0.01% neutral red in PBS is added. This is incubated in the $CO_2$ incubator for 1 hr. The dye is aspirated and the cells are washed using a Nunc Plate Washer. After removing the PBS, 200 μg/well of 50% ETOH/1% glacial acetic acid (in $H_2O$) is added. The plates are rotated for 15 min and the optical densities read at 540 nm on a plate reader. The $EC_{50}$ values are determined by comparing drug treated and untreated cells using a computer program.

Independent cell cytotoxicity tests conducted by or under the direction of Dr. Susan Manly and/or Dr. Samir Ross of the National Center for Natural Products Research (NCNPR) at the University of Mississippi showed the mycelial extracts to be non-toxic at the high levels of exposure in three human cell culture lines. It is therefore possible that the Selectivity Index ratios may be understated, as SI is the CC50 (cytotoxicity) divided by EC (effective concentration) (the amount that limits 50% of the human cell growth rate divided by the amount to kill 50% of the virus). If the SI values are understated, the products described herein could be loaded much higher than that shown before evidence of cytotoxicity would be seen and the actual antiviral activity may be much more than that shown by cell line bioassays described herein. Furthermore, and unexpectedly, the strong antiviral activity is localized by going from ethanol as the first solvent and, after centrifuging and cell-freeing, going to DMSO; samples prepared in this fashion showed antiviral activity whereas samples using water first followed by DMSO consistently failed to show activity. Hence the use of ethanol as a first step is preferred over water. Note that since the living mycelium on sterilized rice has approximately 50% moisture, and hence when equal mass of 99% EtOH is added, the EtOH/Moisture concentration is typically >30%, but <70% at makeup (in contrast, antibacterial activity as reported in the enclosed examples was preserved when water only was used).

The influenza bioassays were conducted according to Sidwell, R W and Smee, D F, *In vitro and in vivo assay systems for study of influenza virus inhibitors*, Antiviral Res., October 2000, 48(1):1-16

All strains below were incubated for approximately two months prior to extractions; some strains were incubated up to 7 months. Activity was seen consistently within this timespan of incubation. With those strains designated as "shaken," the mycelium and ethanol/water were shaken and allowed to settle prior to decanting the extract.

The *Fomitopsis officinalis* strains and extracts described above in Example 1 were utilized. The following codes can be used to decipher the names of the active samples:

Csc: *Cordyceps sinensis*
F.o. I: *Fomitopsis officinalis* Morton, Washington State, USA
F.o. VI: *Fomitopsis officinalis*, Carrington Bay, Cortes Island, British Columbia, Canada
F.o. X: *Fomitopsis officinalis*, Hoh River Valley, Washington State, USA
G. ann.: *Ganoderma annulare*, Cortes Island, B.C., Canada
G.l.: *Ganoderma lucidum*
*G. neojaponicum: Ganoderma neojaponicum*
G.o.: *Ganoderma oregonense*
G.r. *Ganoderma resinaceum* Canada
HDT-3: Mixture of F.o. I, P.b., T.v.
H.e.: *Hericium erinaceous*
H.u.: *Hypsizygus ulmarius*, Canada
Htu: *Hypsizygus ulmarius*
I.o. *Inonotus obliquus*, Quebec, Canada
P.b.: *Piptoporus betulinus*, McCall, Idaho, USA
PhL: *Phellinus linteus*
P.u.: *Polyporus umbellatus*
S.c.: *Schizophyllum commune*
T.v.: *Trametes versicolor*, Kamilche Pt., Washington State, USA 7 Mushroom Blend=A blend of *Agaricus brasiliensis, Cordyceps sinensis, Ganoderna lucidum, Grifola frondosa, Hericium erinaceus, Polyporus umbellatus* and *Trametes versicolor.*

13 Mushroom Blend=A blend of: *Ganoderma resinaceum, Ganoderma applanatum, Ganoderma oregonense, Grifola frondosa, Phellinus linteus, Trametes versicolor, Fomes fomentarius, Fomitopsis officinals, Inonotus obliquus, Lentinula edodes, Polyporus umbellatus*, and *Schizophyllum* commune HD: A 16 mushroom blend of: *Fomitopsis officinalis, Grifola frondosa, Inonotus obliquus,*
*Ganoderma resinaceum, Cordyceps sinensis, Polyporus umbellatus, Piptoporus betulinus, Flammulina velutipes, Agaricus brasiliensis, Phellinus linteus, Schizophyllum commune, Trametes versicolor, Hericium erinaceus, Ganoderma applanatum, Ganoderma oregonense, Fomes fomentarius* and *Lentinula edodes*

HD Fraction 1: A blend of *Grifola frondosa, Flammulina velutipes, Inonotus obliquus, Ganoderna applanatum*

HD Fraction 2: A blend of *Ganoderma resinaceum, Cordyceps sinensis, Phellinus linteus, Ganoderma oregonense*

HD Fraction 2: A blend of *Polyporus umbellatus, Hericium erinaceus, Piptoporus betulinus* and *Lentinula edodes*

INFLUENZA A, MDCK CELL LINE

| | Cmpd Name | Virus | Strain | Assay/Vehicle | Drug Unit | EC50 | IC50 | SI |
|---|---|---|---|---|---|---|---|---|
| 1 | HDT3 1x | Flu A H5N1 | Vietnam 1203 2004H | Visual MEM | Dil. | <0.0001 | >0.1 | >1.000 |
| 2 | Fo-6 25x EtOH only 24 hrs | Flu A H3N2 | Wisconsin 67/2005 | Neutral Red Company Buffer | Dil. | <0.0001 | 0.03 | >260 |
| 3 | Fo-6 25x EtOH only 24 hrs | Flu A H3N2 | Wiscon. 67/2005 | Visual Company Buffer | Dil. | <0.0001 | 0.03 | >320 |
| 4 | Io-1 25x 33 days | Flu A (H5N1) | Vietnam 1203/2004H | Neutral Red DMSO | Dil. | <0.0002 | 0.04 | >200 |
| 5 | Io-1 25x 33 days | Flu A (H5N1) | Vietnam 1203/2004H | Neutral Red DMSO | Dil. | <0.001 | 0.03 | >300 |
| 6 | HD | Flu A (H5N1) | Vietnam 203/2004H | Neutral Red MEM | Dil. | <0.0001 | 0.02 | >200 |
| 7 | HD | Flu A (H5N1) | Vietnam 203/2004H | Visual MEM | Dil. | <0.0001 | 0.03 | >300 |
| 8 | Gr-1 25x | Flu A (H5N1) | Vietnam 203/2004H | Visual DMSO | % | 0.02 | 3.8 | 190 |
| 9 | Io-1 25x | Flu A (H5N1) | Vietnam 203/2004H | Visual DMSO | % | 0.05 | 5.7 | 110 |
| | HDT3 1x | Flu A H5N1 | Vietnam 1203 2004H | Neutral Red MEM | Dil. | 0.01 | >0.1 | >10 |
| | HDT3 1x | Flu A H5N1 | Vietnam 1203 2004H | Neutral Red MEM | Dil. | 0.006 | 0.1 | 17 |
| | HDT3 1x | Flu A H5N1 | Vietnam 1203 2004H | Visual MEM | Dil. | 0.002 | 0.04 | 20 |
| | Fo-6 25x EtOH only 24 hrs | Flu A H3N2 | Vietnam 1203 2004H | Neutral Red DMSO | Dil. | 0.0048 | 0.063 | 13 |

-continued

| INFLUENZA A, MDCK CELL LINE | | | | | | | |
|---|---|---|---|---|---|---|---|
| Cmpd Name | Virus | Strain | Assay/Vehicle | Drug Unit | EC50 | IC50 | SI |
| Fo-6 25x EtOH only 24 hrs | Flu A H3N2 | Vietnam 1203 2004H | Visual DMSO | Dil. | 0.0034 | 0.027 | 7.9 |
| Io-1 25x 33 days | Flu A (H5N1) | Vietnam 1203/2004H | Neutral Red DMSO | Dil. | 0.004 | 0.05 | 10 |
| Io-1 25x 33 days | Flu A (H5N1) | Vietnam 1203/2004H | Neutral Red DMSO | Dil. | 0.004 | 0.06 | 20 |
| HD | Flu A (H5N1) | Vietnam 203/2004H | Neutral Red MEM | Dil. | 0.004 | 0.03 | 8 |
| HD | Flu A (H5N1) | Vietnam 203/2004H | Visual MEM | Dil. | 0.004 | 0.04 | 10 |
| Gr-1 25x | Flu A (H5N1) | Vietnam 203/2004H | Neutral Red DMSO | % | 0.32 | 3.2 | 10 |
| HD Fraction 1 Gf, Ab, Io, Ga | Flu A (H5N1) | Vietnam 203/2004H | Neutral Red DMSO | % | 0.33 | 5.4 | 16 |
| HD Fraction 1 Gf, Ab, Io, Ga | Flu A (H5N1) | Vietnam 203/2004H | Visual DMSO | % | 0.04 | 3.8 | 95 |
| HD Fraction 2 Gf, Ab, Io, Ga | Flu A (H5N1) | Vietnam 203/2004H | Neutral Red DMSO | % | 0.0019 | >0.1 | >53 |
| HD Fraction 2 Gl, Csc, Phl, Go | Flu A (H5N1) | Vietnam 203/2004H | Visual DMSO | % | 0.04 | >0.1 | >25 |
| Pb-1 25x | Flu A (H5N1) | Vietnam 203/2004H | Neutral Red DMSO | % | 0.06 | 2.7 | 45 |
| Pb-1 25x | Flu A (H5N1) | Vietnam 203/2004H | Visual DMSO | % | 0.03 | 1 | 33 |
| PU 1x 23 days | Flu A (H5N1) | Vietnam 203/2004H | Neutral Red DMSO | % | 0.02 | 3 | 20 |
| PU 1x 23 days | Flu A (H5N1) | Vietnam 203/2004H | Visual DMSO | % | 0.1 | 4 | 40 |
| Mycena alcalina | Flu A (H5N1) | Vietnam 203/2004H | Visual DMSO | % | 0.21 | 5.7 | 27 |
| Mycena alcalina | Flu A (H5N1) | Vietnam 203/2004H | Visual CONF DMSO | % | 0.21 | 5.7 | 27 |
| Gr-1 25x | Flu A (H5N1) | Vietnam 203/2004H | Visual DMSO | % | 0.21 | 5.7 | 27 |
| Gr-1 25x | Flu A (H5N1) | Vietnam 203/2004H | Visual CONF DMSO | % | 0.21 | 5.7 | 27 |
| Sc 25x | Flu A (H5N1) | Vietnam 203/2004H | Neutral Red DMSO | Dil. | 0.0067 | >0.1 | >15 |
| HD Fraction 4 Pu, He, Pb, Le | Flu A (H5N1) | Vietnam 203/2004H | Neutral Red DMSO | Dil. | 0.0086 | >0.1 | >12 |
| HD Fraction 4 Pu, He, Pb, Le | Flu A (H5N1) | Vietnam 203/2004H | Visual DMSO | Dil. | 0.0089 | >0.1 | >11 |
| G. ann 25x EtOH only 24 hrs. | Flu A (H5N1) | Vietnam 203/2004H | Neutral Red DMSO | Dil. | 0.0061 | 0.066 | 11 |
| G. ann 25x EtOH only 24 hrs. | Flu A (H5N1) | Vietnam 203/2004H | Visual DMSO | Dil. | 0.0032 | 0.038 | 12 |
| Tv 25x EtOH only 24 hrs. | Flu A (H5N1) | Wisconsin 67/2005 | Visual Company Buffer | Dil. | 0.0028 | 0.032 | 11 |
| Go-4 Elwah EtOH only 2 wks. | Flu A (H3N2) | Vietnam 203.2004H | Visual DMSO | Dil. | 0.0028 | 0.027 | 10 |

| INFLUENZA A RIBAVARIN CONTROL RESULTS AND ACTIVE SAMPLE COMMENTS | | | | | | |
|---|---|---|---|---|---|---|
| | Control Units | Control EC50 | Control EC90 | Control IC50 | Control SI | Comments on active sample |
| 1 | μg/ml | 10 | | >320 | >32 | Moderately to highly active |
| 2 | μg/m1 | 2 | | >320.0000 | >160.00 | Not active by visual but slightly active by neutral |

-continued

| | INFLUENZA A RIBAVARIN CONTROL RESULTS AND ACTIVE SAMPLE COMMENTS | | | | | |
|---|---|---|---|---|---|---|
| | Control Units | Control EC50 | Control EC90 | Control IC50 | Control SI | Comments on active sample |
| | | | | | | red against IVA (H1N1). Highly active against IVA (H3N2). |
| 3 | µg/ml | 1.9 | | >320.0000 | >170.00 | Not active by visual but slightly active by neutral red against IVA (H1N1). Highly active against IVA (H3N2). |
| 4 | µg/ml | 12 | | >320 | >27 | Highly active. |
| 5 | µg/ml | 10 | | >320 | >32 | Highly active. |
| 6 | µg/ml | 12 | | >320 | >27 | Highly active in trial 1, moderately active in trial 2. Storage may have contributed to loss of potency |
| 7 | µg/ml | 10 | | >320 | >32 | Highly active in trial 1, moderately active in trial 2. Storage may have contributed to loss of potency |
| 8 | µg/ml | 3.2 | | >320 | >100 | |
| 9 | µg/ml | 3.2 | | >320 | >100 | |

| | INFLUENZA B, MDCK CELL LINE, ALL ACTIVE SAMPLES DILUTION DRUG UNIT | | | | | | | |
|---|---|---|---|---|---|---|---|---|
| | Compnd Name | Flu B Virus Strain | Assay | Vehicle | EC50 | EC90 | IC50 | SI |
| 1 | Pb-1 25x | Shanghai 361/02 | Neutral Red | DMSO | <0.0001 | | 0.06 | >590 |
| 2 | Gr 25x EtOH only 24 hrs | Shanghai 361/02 | Neutral Red | DMSO | <0.0001 | | 0.04 | >400 |
| 3 | Gr 25x EtOH only 24 hrs | Shanghai 361/02 | Virus Yield | DMSO | | 1E−04 | | 522 |
| 4 | Io-1 25x EtOH only 24 hrs | Shanghai 361/02 | Neutral Red | DMSO | <0.0001 | | 0.04 | >350 |
| 5 | Io-1 25x EtOH only 24 hrs | Shanghai 361/02 | Virus Yield | DMSO | | 1E−04 | | 223 |
| 6 | Fo-13 25x EtOH only 24 hrs | Shanghai 361/02 | Visual | DMSO | 0.0003 | | 0.05 | 150 |
| 7 | Fo-13 25x EtOH only 24 hrs | Shanghai 361/02 | Virus Yield | DMSO | | 1E−04 | | 313 |
| 8 | Fo-13 25x EtOH only 24 hrs | Shanghai 361/02 | Visual-CONF | DMSO | 0.0003 | | 0.05 | 150 |
| 9 | G. ann 25x EtOH only 24 hrs | Shanghai 361/02 | Visual | DMSO | 0.0003 | | 0.06 | 180 |
| 10 | G. ann 25x EtOH only 24 hrs | Shanghai 361/02 | Visual-CONF | DMSO | 0.0003 | | 0.06 | 180 |
| 11 | Fo-10 25x EtOH only 24 hrs | Shanghai 361/02 | Virus Yield | DMSO | | 1E−04 | | 171 |
| 12 | Gr 25x | Shanghai 361/02 | Neutral Red | DMSO | 0.0004 | | 0.05 | 140 |
| | Pb-1 25x | Shanghai 361/02 | Neutral Red | DMSO | 0.0043 | | 0.058 | 13 |
| | Gr 25x EtOH only 24 hrs | Shanghai 361/02 | Neutral Red | DMSO | 0.0023 | | 0.057 | 25 |
| | Gr 25x EtOH only 24 hrs | Shanghai 361/02 | Visual | DMSO | 0.0006 | | 0.047 | 84 |

-continued

INFLUENZA B, MDCK CELL LINE, ALL ACTIVE SAMPLES DILUTION DRUG UNIT

| Compnd Name | Flu B Virus Strain | Assay | Vehicle | EC50 | EC90 | IC50 | SI |
|---|---|---|---|---|---|---|---|
| Io-1 25x EtOH only 24 hrs | Shanghai 361/02 | Neutral Red | DMSO | 0.0021 | | 0.057 | 11 |
| Io-1 25x EtOH only 24 hrs | Shanghai 361/02 | Visual | DMSO | 0.0006 | | 0.047 | 52 |
| Fo-13 25x EtOH only 24 hrs | Shanghai 361/02 | Neutral Red | DMSO | 0.0012 | | 0.054 | 45 |
| Io-1 25x | Shanghai 361/02 | Neutral Red | DMSO | 0.001 | | 0.057 | 57 |
| Io-1 25x | Shanghai 361/02 | Virus Yield | DMSO | 0.001 | | 0.057 | 57 |
| Pb-1 25x | Shanghai 361/02 | Neutral Red | DMSO | 0.0013 | | 0.051 | 39 |
| Pb-1 25x | Shanghai 361/02 | Neutral Red | DMSO | 0.0024 | | 0.058 | 24 |
| Pb-1 25x | Shanghai 361/02 | Visual | DMSO | 0.0015 | | 0.038 | 25 |
| Pb-1 25x | Shanghai 361/02 | Virus Yield | DMSO | | 0.001 | | 27 |
| Pb-1 25x | Shanghai 361/02 | Virus CONF | DMSO | 0.0015 | | 0.038 | 25 |
| Tv EtOH 24 hrs. | Shanghai 361/02 | Neutral Red | DMSO | 0.0012 | | 0.042 | 35 |
| Pu 25x | Shanghai 361/02 | Visual | DMSO | 0.0011 | | 0.038 | 35 |
| Pu 25x | Shanghai 361/02 | Virus yield | DMSO | | 0.002 | | 23 |
| Pu 25x | Shanghai 361/02 | Visual CONF | DMSO | 0.0011 | | 0.038 | 35 |
| Sc 25x | Shanghai 361/02 | Visual | DMSO | 0.0032 | | >0.1 | >31 |
| Sc 25x | Shanghai 361/02 | Virus yield | DMSO | | 0.003 | | >31 |
| Sc 25x | Shanghai 361/02 | Visual CONF | DMSO | 0.0032 | | >0.1 | >31 |
| PhL 25x | Shanghai 361/02 | Neutral Red | DMSO | 0.007 | | >0.1 | >14 |
| PhL 25x | Shanghai 361/02 | Visual | DMSO | 0.0032 | | >0.1 | >31 |
| PhL 25x | Shanghai 361/02 | Visual CONF | DMSO | 0.0032 | | >0.1 | >31 |
| G. neo japonicum EtOH only 2 wks | Malaysia 2506/2004 | Visual | DMSO | 0.0024 | | 0.05 | 21 |
| Hu 1x | Shanghai 361/02 | Neutral Red | DMSO | 0.0072 | | 0.1 | 14 |
| Hu 1x | Shanghai 361/02 | Visual | DMSO | 0.0089 | | 0.1 | 11 |
| Mycena alcalina | Shanghai 361/02 | Visual | DMSO | 0.41 | | 5.7 | 14 |
| HD | Shanghai 361/02 | Neutral Red | DMSO | 0.0073 | | 0.093 | 13 |
| Go EtOH only 2 wks. | Malaysia 2506/2004 | Visual | DMSO | 0.0043 | | >0.05 | >12 |
| GI 34D EtOH only 2 wks. | Malaysia 2506/2004 | Visual | DMSO | 0.0028 | | 0.028 | 10 |
| 13 Mushroom Blend | Shanghai 361/02 | Visual | DMSO | 0.7 | | 6 | 8.6 |
| 13 Mushroom Blend | Shanghai 361/02 | Neutral Red | DMSO | 0.3 | | 3 | 10 |

INFLUENZA B RIBAVARIN CONTROL RESULTS AND ACTIVE SAMPLE COMMENTS

| | Control Units | Control EC50 | Control EC90 | Control IC50 | Control SI | Comments on active sample |
|---|---|---|---|---|---|---|
| 1 | µg/ml | 7.1 | | >320.0000 | >45.0000 | Highly active. |
| 2 | µg/ml | 7.1 | | >320.0000 | >45.0000 | Highly active. |
| 3 | µg/ml | | 37.72 | | >8.4000 | Moderately to highly active as confirmed by VYR assay. |
| 4 | µg/ml | 7.1 | | >320.0000 | >45.0000 | Highly active. |
| 5 | µg/ml | | 37.72 | | >8.4000 | Moderately to highly active as confirmed by VYR assay. |
| 6 | µg/ml | 1.7 | | >320.0000 | >190.0000 | Moderately to highly active. |
| 7 | µg/ml | | 37.72 | | >8.4000 | Moderately to highly active as confirmed by VYR assay. |
| 8 | µg/ml | 1.7 | | >320.0000 | >190.0000 | Moderately to highly active as confirmed by VYR assay. |
| 9 | µg/ml | 1.7 | | >320.0000 | >190.0000 | Moderately to highly active. |
| 10 | µg/ml | 1.7 | | >320.0000 | >190.0000 | Moderately to highly active as confirmed by VYR assay. |
| 11 | µg/ml | | 37.72 | | >8.4000 | Moderately to highly active as confirmed by VYR assay. |
| 12 | µg/ml | 7.1 | | >320.0000 | >45.0000 | Highly active. |

HERPES SIMPLEX VIRUS

| Cmpd Name | Virus | Assay | Cell Line | Drug Unit | EC50 | EC90 | CC50 | SI | ACVEC50 | Comment |
|---|---|---|---|---|---|---|---|---|---|---|
| Fo-1 25x EtOH only 3 weeks | HSV-1 | CPE | HFF cells | % sol | .02 | >1 | 3.9 | 195 | 0.3 | HSV-1 and HSV-2 PR |
| G. ann 25x cold water only 24 hrs | HSV-1 | CPE | HFF cells | % sol | 0.8 | 17.8 | >25 | >31.2 | 1.2 | |
| Fo-1 25x EtOH only 3 weeks | HSV-2 | CPE | HFF cells | % sol | 0.15 | >1 | 3.9 | 26 | 0.2 | HSV-1 AND HSV-2 PR |
| Tv 25x room water only 24 hrs | HSV-2 | CPE | HFF cells | % sol | 0.7 | >5 | 16.8 | 24 | 0.2 | Drug residue stained very darkly |

HCV Virus, Huh7 ET Cell Type, Drug Units Fold Dilution

| | | | Primary Assay | | | Confirmatory Assay | | | | | |
|---|---|---|---|---|---|---|---|---|---|---|---|
| ID | Assay and Assay Type | High Test Conc. | Actvty % inhib. virus control | Cyto-toxicity % cell control | SI | EC50 | EC90 | IC50 | IC90 | SI50 | SI90 |
| Csc 25x | HCV RNA replicon Single Dose Primry | 100 | 85.6 | 11.8 | <1 | | | | | | |
| Csc 25x | HCV RNA replicon/ Confirmatory dose respnse | 100 | | | | .62 | 5.62 | 0.6 | >100 | .96 | >17.8 |
| Fo-10 | HCV RNA | 100 | 94.9 | 0.7 | <1 | | | | | | |

-continued

| HCV Virus, Huh7 ET Cell Type, Drug Units Fold Dilution | | | | | | | | | | | |
|---|---|---|---|---|---|---|---|---|---|---|---|
| | | | Primary Assay | | | | | | | | |
| | Assay and Assay | High Test | Actvty % inhib. virus | Cyto-toxicity % cell | | Confirmatory Assay | | | | | |
| ID | Type | Conc. | control | control | SI | EC50 | EC90 | IC50 | IC90 | SI50 | SI90 |
| 25x cold water 24 hrs | replicon Single Dose Primry | | | | | | | | | | |
| Fo-10 25x cold water 24 hrs only | HCV RNA replicon/ Confirmatory dose respnse | 100 | | | | 52.1 | >100 | 59.6 | 90.9 | 1.14 | 0.91 |
| Fo-10 25x cold water 24 hrs only | HCV RNA replicon Single Dose Primry | 100 | 94.9 | 0.9 | <1 | | | | | | |
| Fo-10 25x cold water 24 hrs only | HCV RNA replicon/ Confirmatory dose respnse | 100 | | | | 35.7 | 95.2 | 62.6 | 92.5 | 1.8 | 0.97 |
| IFN alpha-2b | HCV RNA replicon Single Dose Primry | 2 | 94.7 | 95.1 | >1 | | | | | | |
| IFN alpha-2b | HCV RNA replicon/ Confirmatory dose respnse | 2 | | | | 0.12 | 0.54 | >2.0 | >2.0 | >16.7 | >3.7 |
| Tv EtOH only 24 hours | HCV RNA replicon Single Dose Primry | 100 | 85.6 | 81.6 | >1 | | | | | | |
| Tv EtOH 24 hours | HCV RNA replicon/ Confirmatory dose respnse | 100 | | | | 5.59 | >100 | >100 | >100 | >17.9 | >1 |
| IFN alpha-2b | HCV RNA replicon Single Dose Primry | 2 | 85.6 | 81.6 | >1 | | | | | | |
| IFN alpha-2b | HCV RNA replicon/ Confirmatory dose respnse | 2 | | | | 0.07 | 0.38 | >2 | >2 | >28.6 | >5.26 |

| Bacteria | Mushroom Extracts-% Inhibition<br>*Fomitopsis officinalis* | 7 Mushroom Blend | 13 Mushroom Blend | HD 16 Mushroom Blend |
|---|---|---|---|---|
| *Mycobacterium tuberculosis* | 73% | 63% | 70-87% | 63% |

| Top Results Against Viruses from Mushroom Extract Samples | | |
|---|---|---|
| Extract | Preparation | SI |
| Results for *Mycobacterium tuberculosis* | | |
| Fo-1 25x | EtOH only 3 weeks | Active<br>IC90 = 0.981<br>IC50 = 0.888 |

Example 4

Water only, room temperate, cell free, centrifuged extracts from live mycelium were prepared. The following codes define the active samples and species being employed:

| Identification Number | Species |
|---|---|
| ES-100 | F.f. |
| ES-101 | G.o. |
| ES-102 | HTU |
| ES-103 | P.o. |
| ES-104 | T.v. |
| ES-105 | F.o. X |
| ES-106 | G.r. |
| ES-107 | I.o. |
| ES-108 | P.b. I |
| ES-109 | T.v. |

Note that the scales in the following charts are logarithmic (base 10), and CFU's are "colony forming units". Reductions of significance vary from ~10:1 to 10,000,000:1 over 72 hours of exposure of the bacteria *E. coli* and *Staphylococcus aureus*.

The basic procedure used for the *E. coli* and *S. aureus* bioassay was: AOAC International 2000, AOAC official method 960.09, p. 10. In P. Cunniff (ed.), Official methods of analysis of AOAC International, 17th ed. AOAC International, Gaithersburg, Md.

The cultures used were obtained from ATCC, *E. coli* O157:H7: 35150 and *S. aureus:* 12600. The antimicrobial efficacy of the fungal extracts of live mycelium were tested on the growth profile of *E. coli* O157:H7 and *Staphylococcus aureus:* 12600.

Materials and Methods

Preparation of Cultures

*E. coli* O157:H7 and *Staphylococcus aureus:*12600 strains obtained from ATCC were used to generate inocula. Strains available as frozen (−80° C.) stock cultures in tryptic soy broth (Becton Dickinson, Sparks, Md.) with 20% glycerol and were activated by inoculating both the strains in tryptic soy broth (TSB) and incubating at 35±2° C. for 72 h. Cultures were streaked on tryptic soy agar with 5% blood (TSA II 5% SB, Becton Dickinson) and incubated at 35±2° C. for 48 h. Colonies from each organism were suspended in phosphate-buffered saline (PBS; pH 7.4; 0.2 g $KH_2PO_4$, 1.5 g $Na_2HPO_4.7H_2O$, 8.0 g NaCl and 0.2 g KCl in 1 L distilled water) to yield a suspension concentration of approximately 108 cells/ml.

Treatments

Ten fungal extracts were evaluated for their antimicrobial efficacy on the growth of *E. coli* O157:H7 and *S. aureus* for this study. The various fungal extracts evaluated for the study included: ES-100 to ES-109. For each compound, different concentrations (0, 1, 10, and 100%) were prepared by diluting the stock with sterile buffered peptone water. A 1-ml portion of each actively growing culture was placed into 9 ml of sterile buffered peptone water containing fungal extract with different pre-determined concentrations. Samples were stored at room temperature and were drawn after 24, 48, and 72 hours following which microbiological analysis was performed. All the experiments were replicated three times.

Experimental Design and Statistical Analysis

The treatments were designed using a randomized complete block design (RCBD). The organisms were treated as blocks and within each block the effect of compound, concentration, and time of contact was evaluated on the growth profile of the organism. The data was analyzed using analysis of variance (ANOVA) using the PROC GLM procedure available in SAS software. The effect of a treatment (concentration or time of contact or compound) was deemed significant at alpha=0.05.

Microbiological Analysis

Both untreated and treated samples were analyzed to determine the bacterial load prior to and after treating. Serial dilutions were made using standard microbiological practices and the serial dilutions thereof (0.1 ml) were surface plated onto blood agar. Plates were incubated at 35±2° C. for 24 h before the colonies were counted.

Results and Discussion

Effect of the Fungal Extracts on the Survival of *E. coli* O157:H7

Figure 2:
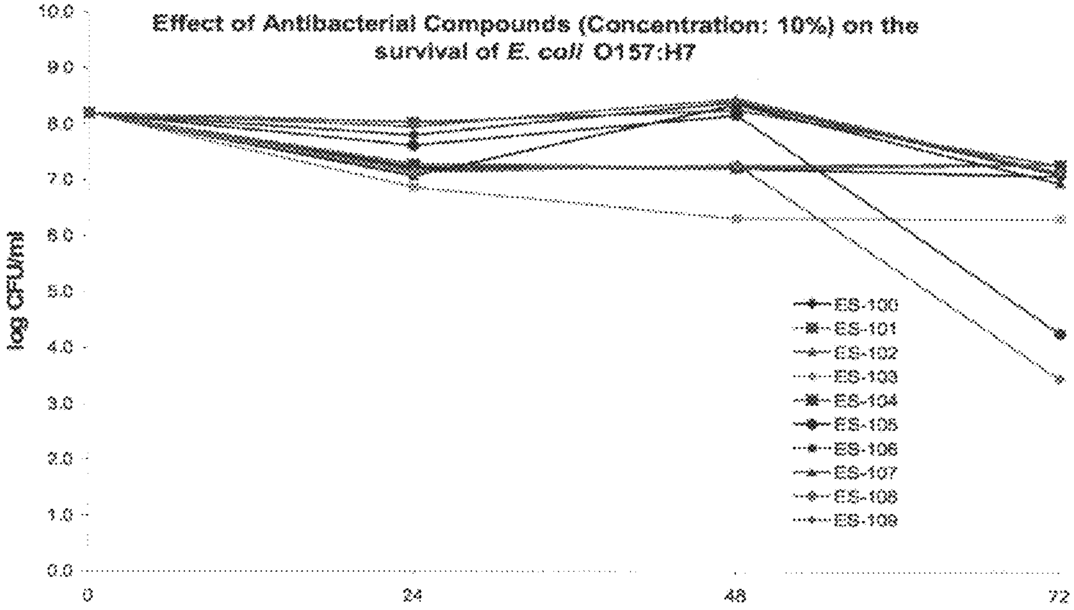
FIG. 2 is a chart showing the effect of antibacterial compounds (concentration: 10%) on the survival of *E. coli* O157:H7.
Figure 3:
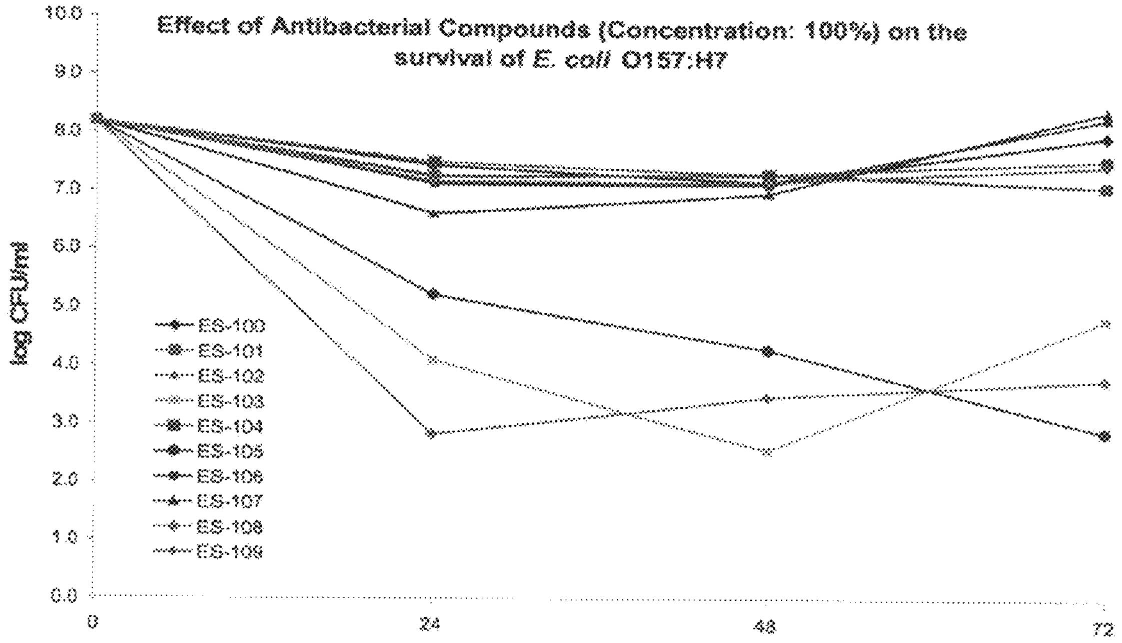
FIG. 3 is a chart showing the effect of antibacterial compounds (concentration: 100%) on the survival of *E. coli* O157:H7.

Fungal extracts varied significantly ($P<0.05$) in their antimicrobial effect against *E. coli* O157:H7. Similarly concentration and time of storage had a significant ($P<0.05$) effect on the survival of *E. coli* O157:H7. FIGS. 1-3 summarize the effect of various fungal extract compounds on the survival of *E. coli* O157:H7. In general, reductions of *E. coli* O157:H7 due to fungal extract treatments decreased as follows: ES-103=ES108>ES-105>ES-100=ES-104=ES-102>ES-101=ES-107=ES-109=ES-106. Overall the antibacterial effect increased with increase in concentration of the compound. The antibacterial activity of the compounds was maximum at 100% followed by 10% and 1%. In general, ES-103, ES-105, and ES-108 demonstrated the maximum antibacterial activity on *E. coli* O157:H7. At the end of 72 h of storage, ES-105 and ES-108 caused approximately 4-5 log reduction of *E. coli* O157:H7 when applied at a concentration of 10% and 100%. ES-103 also caused a 4 log reduction ($P<0.05$) of *E. coli* O157:H7 but only when applied at 100%.

See FIG. 1, Effect of Antibacterial Compounds (Concentration: 1%) on the survival of *E. coli* O157:H7

See FIG. 2, Effect of Antibacterial Compounds (Concentration: 10%) on the survival of *E. coli* O157:H7

See FIG. 3, Effect of Antibacterial Compounds (Concentration: 100%) on the survival of *E. coli* O157:H7

Effect of the Fungal Extracts on the Survival of *S. aureus*

Figure 4:
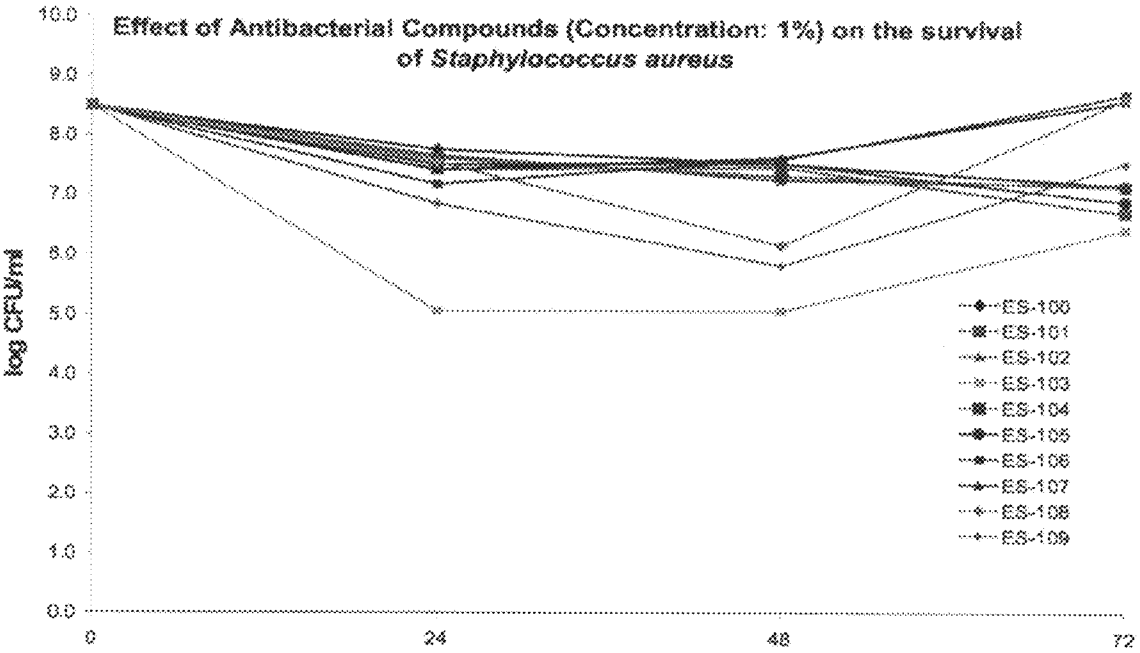
FIG. 4 is a chart showing the effect of antibacterial compounds (Concentration: 1%) on the survival of *Staphylococcus aureus*.
Figure 5:
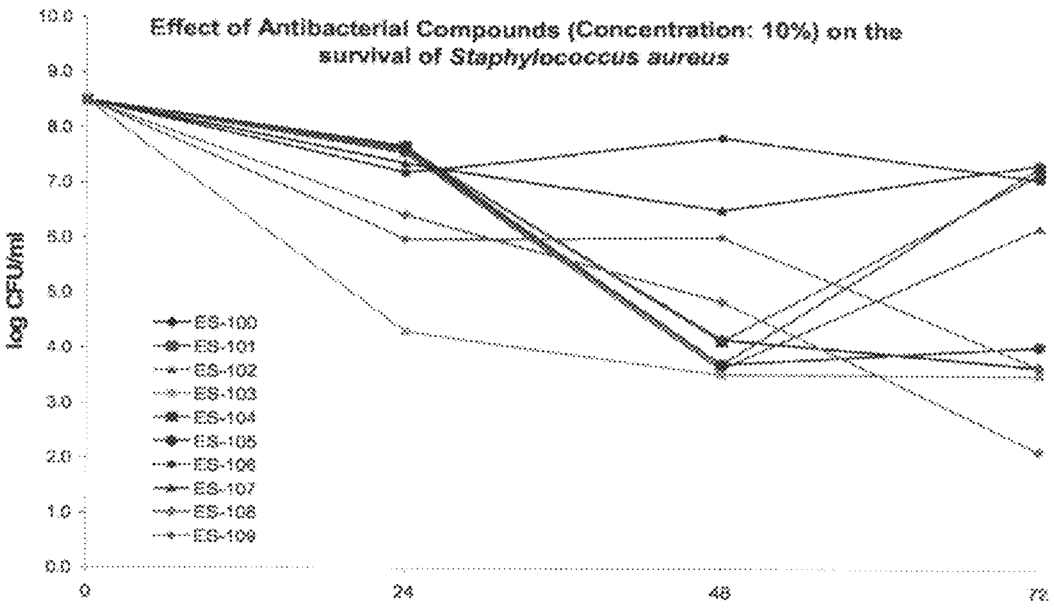
FIG. 5 is a chart showing the effect of antibacterial compounds (Concentration: 10%) on the survival of *Staphylococcus aureus*.
Figure 6:
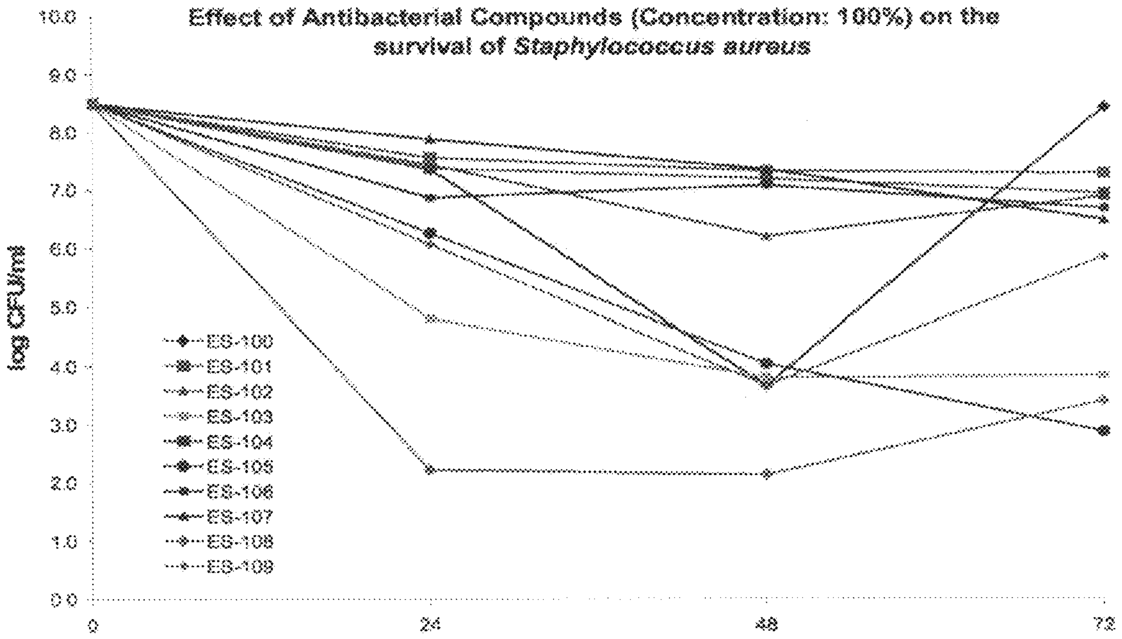
FIG. 6 is a chart showing the effect of antibacterial compounds (Concentration: 100%) on the survival of *Staphylococcus aureus*.

Fungal extracts varied significantly ($P<0.05$) in their antimicrobial effect against *S. aureus*. Similarly concentration and time of storage had a significant ($P<0.05$) effect on the survival of *S. aureus*. FIGS. 4-6 summarize the effect of various fungal extract compounds on the survival of *S. aureus*. In general, reductions of *S. aureus* due to fungal extract treatments decreased as follows: ES-103=ES108>ES-105=ES-109>ES102>ES-101>ES-100=ES-104=ES-107>ES=106. Overall, the antibacterial effect increased with increase in concentration of the compound. The antibacterial activity of the compounds was maximum at 100% followed by 10% and 1%. In general, ES-103, ES-105, ES-108 and ES-109 demonstrated the maximum antibacterial activity on *S. aureus*. At the end of 72 h of storage ES-103, ES-105 and ES-108 caused approximately 4-5 log reduction of *S. aureus* when applied at a concentration of 100%. At the end of 72 h of storage ES-103, ES-105, ES-108, and ES-109 caused approximately 4-6 log reduction of *S. aureus* when applied at a concentration of 10%. At the end of 48 h of storage ES-109 caused approximately 5-log reduction ($P<0.05$) of *S. aureus* when applied at 100%; however, at the end of 72 h of storage, *S. aureus* increased by approximately 3 log CFU/ml.

See FIG. 4, Effect of Antibacterial Compounds (Concentration: 1%) on the survival of *Staphylococcus aureus*

See FIG. 5, Effect of Antibacterial Compounds (Concentration: 10%) on the survival of *Staphylococcus aureus*

See FIG. 6, Effect of Antibacterial Compounds (Concentration: 100%) on the survival of *Staphylococcus aureus*

CONCLUSIONS

Fungal extracts varied in their antibacterial effect on *E. coli* O157:H7 and *S. aureus*.

*S. aureus* was more sensitive to the fungal extracts than *E. coli* O157:H7

ES-105 (*Fomitopsis officinalis*) and ES-108 (*Piptoporus betulinus*) caused approximately 4-5 log reduction of *E. coli* O157:H7 at the end of 72 h of storage when applied at a concentration of 10% and 100%.

ES-103 (*Pleurotus ostreatus* from "bunker burlap bags") also caused a 4 log reduction ($P<0.05$) of *E. coli* O157:H7 but only when applied at 100%.

ES-103 (*Pleurotus ostreatus* from "bunker burlap bags"), ES-105 (*Fomitopsis officinalis*) and ES-108 (*Piptoporus betulinus*) caused approximately 4-5 log reduction of *S. aureus* at the end of 72 h of storage when applied at a concentration of 100%. At the end of 72 h of storage ES-103, ES-105, ES-108, and ES-109 (*Trametes versicolor*) caused approximately 4-6 log reduction of *S. aureus* when applied at a concentration of 10%.

At the end of 48 hours of storage ES-109 (*Trametes versicolor*) caused approximately 5-log reduction ($P<0.05$) of *S. aureus* when applied at 100%; however, at the end of 72 h of storage, *S. aureus* increased by approximately 3 log CFU/ml.

From these data showing direct antiviral and antibacterial activity, it is reasonably predictable and expected that the compositions will have utility in humans in preventing, treating, alleviating, ameliorating, mitigating, reducing and/or curing infection and/or symptoms from viruses, including smallpox.

When the mycelial extracts were dried and fractionated, none of the 91 fractions showed any antiviral activity at the concentrations tested and yet the whole extracts continued to show significant antiviral activity, repeatedly and consistently, for more than two years from creation.

GC testing of the *Fomitopsis* and *Piptoporus* extracts for agaric acid showed no agaric acid to be present. It will be noted that the activity of agaric acid does not correlate well with the activity of the extracts in the bioassays herein. HPLC analysis of the *Fomitopsis* and *Piptoporus* extracts showed no betulinic acid to be present. It is, of course, possible that agaric acid and/or betulinic acid may be an intermediate in various cellular processes or may be found to be biologically incorporated into various cellular constituents. It is further possible that such molecular matrices may serve to detoxify the cytotoxicity while preserving antiviral properties. However, it does not appear that the antiviral properties of the present invention may be ascribed to either agaric acid or betulinic acid and it is expected that the extracts possess novel antiviral and antimicrobial compounds.

Although ethanol was used as the organic solvent, ethanol is clearly not the causal agent, as numerous samples of other mushroom species showed no activity although they were also presented in the same form (ethanol and water) as was *Fomitopsis officinalis*. The present compositions provide antiviral activity that is due to contact with mycelial components beyond any effect due to contact with the ethanol, provide compositions wherein the survivability of the viruses is limited upon contact with the extract while selectively not harming healthy human cells.

The compositions are preferably extracted with ethanol, water or combinations thereof and the extracts are more preferably extracted with cold, room temperature or warm solvent. Not as preferred is hot or boiling solvent.

Novel aspects of the present invention include antiviral and antibacterial effect with extracts, as a topical disinfectant, i.e. topical surfaces, including cultures of organisms.

Extracts made from the mycelium are active; extracts from the mushroom are not active or not as active.

Purification of the active antivirals "appear" to be extracted with EtOH but not with $H_2O$ only. Purification of the active antibacterials "appear" to be extracted with $H_2O$ but not with EtOH. No adverse reactions from human ingestion. Water only extracts of F.o, P.b., T.v., I.o. and P.o. are antibacterial; ethanol only extracts of F.o., P.b., T.v., G.r., G.ann., H.u., HTU and I.o. are antiviral. Heat is believed to destroy most antiviral activity; cold temperature or room temperature extraction is preferred.

Anti-infective agents from medicinal mushrooms and mushroom mycelia: adjuncts to immunotherapy and potentiating host defense for disease resistance. This coincides with the many anecdotal reports of the extracts helping fight infection in wounds and aiding in wound-healing. Having a treatment that is both anti-staph/anti-*E. Coli* and anti-viral is uniquely important.

Solving the *Staph. aureus* problem solves many collateral problems in the hospital. Since so many battlefield wounds are *staph*-prone, and since anesthesia suppresses the immune system, making patients more susceptible to infection, and since viral infections are often complicated by subsequent bacterial infections, fungal extracts as disclosed herein may be particularly important for protecting citizens and soldiers.

*E. coli* contamination on spinach, lettuce or other crops may re reduced, alleviated or eliminated by treatment with the disclosed fungal extracts. The reduction in *E. coli* is enough to address human food concerns, including organic food producers concerns. A food grade spray on treatment for vegetables and a topical spray for food preparation surfaces.

Having an extract/compound that is dually anti-bacterial and antiviral is especially useful.

Topical, antibacterial effects from using water-only extracts of mycelium at room temperature. My hypothesis is this is the window in which mycelium has evolved for millions of years, and within this window we will find activity, whereas hot-water extraction is likely (not proven yet) to destroy anti-bacterial compounds.

Since *E. coli* is an endospore-forming bacterium, and commonly used as a surrogate for *Bacillus anthracis*, aka 'anthrax' this invention anticipates that fungal preparations and combinations thereof found effective at reducing CFU (colony forming units) of *E. coli* may also prove useful at inhibiting the germination and growth of *Bacillus anthracis*, thus lessening its severity of infection, or its infectivity.

Having a convenient, readily applied throat spray utilizing the antivirally active mushroom preparations described here, having anti-flu (including H5N1), anti-pox (Variola major), anti-SARS as well as antibacterially active mushroom preparations useful for preventing infections from TB (tuberculosis causing organisms such as *Mycobacterium tuberculosis* and *Mycobacterium intracellulare*), can help protect passengers traveling on airplanes, trains, passenger ships, automobiles, as well as where any groups of people congregate, from these and other types of infectious diseases.

Infections from *Staphylococcus aureus*, particularly MRSA (Methicillin Resistant Strains of *Staphylococcus aureus*) complicate recovery from surgical operations. Having a topically applied anti-infective compounded with a disinfectant such as ethanol can be helpful for patient health worldwide.

Another potentially useful application of this invention is the topical application in the form of a spray upon foodstuffs, including vegetables and meats prone to spoilage by *E. coli*. and/or other organisms. Different than a disinfectant which can immediately destroy problematic bacteria, for instance, the spray envisioned within this invention has residual anti-*E. coli* and anti-bacterial properties, so that colonies of bacteria that do survive the initial exposure to a disinfectant are retarded in their subsequent growth due to the longer lasting effects of the mycelially derived spray. Similarly, the spray's anti-fungal, antibacterial and anti-protozoal properties make it an ideal candidate for extending shelf life of any material that is otherwise degraded or made less useful by colonizing organisms. This novelty also has applications for wound-healing, allowing new tissue to grow without the stifling effects of problematic bacteria such as *Staphylococcus aureus*. Repeated applications of such a spray combined with a disinfectant like alcohol doubly enables the usefulness of this invention.

The extract may be mixed with glycerin to give fifty-fifty EtOH-glycerin, then placed under vacuum (2 C. to 10 C.) to remove the alcohol and give a glycerin extract.

Similar antimicrobial/antifungal activity is expected for *Candida albicans, Cryptococcus neoformans, Escherichia coli, Pseudomonas aeruginosa, Mycobacterium intracellulare* and *Aspergillus fumigatus*, and similar antiparasitic activity is expected for *Plasmodium falciparum* and *Leishmania donovani*. Activity is also expected against Ebola and *Streptococcus pyogens*.

An anticipated method of extraction will be to take the ethanol extract and using compressed liquid carbon dioxide wash the EtOH extract under pressure, removing the EtOH, and then once the EtOH is removed, the liquid carbon dioxide is then evacuated. Once the liquid carbon dioxide vaporizes and this liquid carbon dioxide is removed, the antivirally-active and anti-bacterially active agents are reduced into a dried form, thus allowing further potentiation and purification, and this reduction becomes more useful in a wider array of delivery systems for medicines. Methanol and acetone wash of mycelium by carbon dioxide may also be utilized, optionally using a critical point dryer.

The best solvent to use for viruses is apparently EtOH except for Hepatitis C(HCV). The preferred extraction temperature for antivirals is 2 C. For antibacterial and antiviral extracts, an extraction time of 24 hours or 3 weeks is preferred, or an intermediate time. Extracts are preferably utilized when fresh as antibacterial and antiviral activity may degrade with time.

Another example of anticipated extraction is with mycelium grown on rice to optimize CFU's, immerse by equal mass into 99 percent EtOH, filter, centrifuge, discard precipitate, cell-free filter, and use.

It will be understood that a supplement or extract composed of ingredients from the fungi *Fomitopsis officinalis, Fomitopsis pinicola, Piptoporus betulinus, Ganoderma resinaceum, G. lucidum, G. annulare, Trametes versicolor, Inonotus obliquus, Hypsizygus ulmarius, Hypsizygus tessulatus* and/or other species of the genera can be used in an amount sufficient to the have the effect of preventing, treating, mitigating, reducing, alleviating, ameliorating or curing infection from viruses or their vectors, including Cowpox, Variola (smallpox) and other Orthopox viruses, coronaviruses including SARS, HIV, influenza, avian influenza, Venezuelan Equine Encephalitis, Yellow fever, West Nile, SARS, Rhinovirus New World and Old World arenaviruses including the American hemorrhagic fevers, Lassa and lymphocytic choriomeningitis, VEE, Hantavirus, Rift Valley fever, sandfly fever, yellow fever, West Nile, Dengue fever, respiratory viruses, Rhinoviruses, Herpes Simplex I, Herpes Simplex II, Lyme, HELA, Epstein Barr, Ebola, Varicella-Zoster, adenoviruses, Polio, Hepatitis including Hepatitis A, B and C, and/or from the microbes causing Tuberculosis, pneumonia (bacterial pneumonia, viral pneumonia, and *mycoplasma* pneumonia), such as *Plasmodium falciparum, Listeria, Pneumococcus, Bacillus anthracis, Escherichia coli, Mycobacterium tuberculosis*, bacteriophages and fungi such as *Candida albicans* should be obvious to one skilled in the art and considered within the scope of the invention. As the products and methods of the present invention treat both viruses and opportunistic pathogenic organisms such as *Mycobacterium tuberculosis* and other bacteria, it will be appreciated that the present invention is exceptionally advantageous insofar as viral infections can lead to bacterial infections and vice versa.

It will also be obvious to one skilled in the art that isolation, fractionation, purification and/or identification of DNA, RNA and protein sequences responsible for antiviral activity and antiviral agents from *Fomitopsis officinalis, Fomitopsis pinicola, Piptoporus betulinus, Ganodemma resinaceum* or the other fungal species disclosed herein could be transferred to another organism, such as a bacterium or yeast, for the commercial production of antiviral agents and/or its antiviral or antimicrobial active derivatives and should be considered within the scope of the invention. It is to be expected that derivative to this invention will lead to the discovery of active ingredients (AI's) which can be used to identify, isolate, concentrate and allow for modification from suites of fungal strains in search for hyperproducers. Upon discovery of the genes responsible for expression of AI's, these genes can be recopied multiple times into the DNA of yeasts, bacteria, and other organisms allowing for further increases in production of a valuable medicine while lowering costs.

The publications and other materials used herein to illuminate the background of the invention and in particular cases, to provide additional details respecting the practice, are incorporated by reference.

It should be understood the foregoing detailed description is for purposes of illustration rather than limitation of the scope of protection accorded this invention, and therefore the description should be considered illustrative, not exhaustive. The scope of protection is to be measured as broadly as the invention permits. While the invention has been described in connection with preferred embodiments, it will be understood that there is no intention to limit the invention to those embodiments. On the contrary, it will be appreciated that those skilled in the art, upon attaining an understanding of the invention, may readily conceive of alterations to, modifications of, and equivalents to the preferred embodiments without departing from the principles of the invention, and it is intended to cover all these alternatives, modifications and equivalents. Accordingly, the scope of the present invention should be assessed as that of the appended claims and any equivalents falling within the true spirit and scope of the invention.

I claim:

1. A composition for restricting the growth, spread and survivability of a virus comprising an aqueous ethanol extract of a mycelium of a medicinal mushroom wherein the virus is selected from the group consisting of influenza, including influenza A H5N1 and H3N2 and influenza B, avian influenza and Herpes Simplex I and II, wherein the medicinal mushroom is *Fomitopsis officinalis* and wherein the extract has a selectivity index ($SI=CC_{50}/EC_{50}$) against the virus ≥10.

2. The composition of claim 1, wherein the mycelium is selected from the group consisting of live mycelium, dried mycelium, freeze dried mycelium or a combination thereof.

3. The composition of claim 1, wherein the aqueous ethanol extract is administered in a form selected from the group consisting of orally-active powders, pills, capsules, teas, extracts, dried extracts, sublinguals, sprays, dispersions, solutions, suspensions, emulsions, foams, syrups, lotions, ointments, gels, pastes, dermal patches, injectables, vaginal creams and suppositories.

4. The composition of claim 1, wherein the composition additionally comprises a mycelial extract selected from the group consisting of, *Ganoderma resinaceum* and *G. annulare* extracts, *Inonotus obliquus* extracts, *Hypsizygus ulmarius* and *H. tessulatus* extracts and *Trametes versicolor* extracts.

5. The composition of claim 1, wherein the extract inhibits bacteria selected from the group consisting of *Escherichia coli* and *Staphylococcus aureus*.

6. The composition of claim 2, wherein the live mycelium is grown on a grain.

7. A composition comprising an aqueous ethanol extract of *Fomitopsis officinalis* mycelium wherein the extract has an antiviral activity Selectivity Index ($SI=CC_{50}/EC_{5}O$) against flu viruses that is ≥10 and the survivability of the flu viruses is limited upon contact with the extract of *Fomitopsis officinalis*.

8. A composition for limiting the survivability of flu viruses upon contact with the composition while selectively not harming healthy human cells comprising an aqueous ethanol extract of live *Fomitopsis officinalis* mycelium wherein the extract has a Selectivity Index ($SI=CC_{50}/EC_{50}$) against a flu virus that is ≥10.

9. A composition for limiting the susceptibility of human cells to infection by a flu virus, wherein the composition contacts the flu virus prior to the flu virus contacting said cells, and wherein the composition comprises an aqueous ethanol extract of *Fomitopsis officinalis* mycelium with a calculated Selectivity Index ($SI=CC_{50}/EC_{50}$) against a flu virus that is ≥10.

10. A composition for restricting the growth, spread and survivability of a virus comprising an aqueous ethanol *Fomitopsis officinalis* extract, wherein the virus is an influenza virus, and wherein the influenza virus is an influenza virus selected from the group consisting of: influenza A H5N1 and H3N2, influenza B and avian influenza, and wherein the extract has a selectivity index (SI) against the influenza >100.

11. The composition of claim 10, wherein the mycelium of a mycelium of a *Fomitopsis* medicinal mushroom is selected from the group consisting of live mycelium, dried mycelium, freeze dried mycelium or a combination thereof.

12. The composition of claim 10, wherein the composition additionally comprises a mycelial extract selected from the group consisting of, *Ganoderma resinaceum* and *G. annulare* extracts, *Inonotus obliquus* extracts, *Hypsizygus ulmarius* and *H. tessulatus* extracts and *Trametes versicolor* extracts.

13. The composition of claim 10, wherein the live mycelium is grown on a grain.

14. A composition for restricting the growth, spread and survivability a virus comprising an aqueous ethano extract of a medicinal mushroom mycelium wherein the virus is selected from the group consisting of influenza, wherein the influenza is influenza A H5N1 and H3N2, Influenza B, or avian influenza, or Herpes Simplex I and/or II, wherein the medicinal mushroom mycelium is *Fomitopsis officianalis* and wherein the extract has a selectivity index (SI) against the virus ≥10 and inhibits bacteria, wherein the bacteria is selected from the group consisting of *Stapylococcus aureaus* and *Escheria coli*, and wherein inhibition of the bacteria is greater than 99%.

15. The composition of claim 14, wherein the mycelium is selected from the group consisting of live mycelium, dried mycelium, freeze dried mycelium or a combination thereof.

16. A composition for restricting the growth, spread and survivability of a virus comprising an aqueous ethanol extract of a medicinal mushroom mycelium wherein the virus is influenza, wherein the medicinal mushroom mycelium is *Fomitopsis officinalis* mycelium and wherein the aqueous ethanol extract has a selectivity index (SI) against influenza ≥10 and inhibits bacteria selected from the group consisting of *Stapylococcus aureaus* and *Escheria coli*, and wherein inhibition of the bacteria is greater than 99%.

17. The composition of claim 16, wherein the mycelium is selected from the group consisting of live mycelium, dried mycelium, freeze dried mycelium or a combination thereof.

* * * * *